(12) United States Patent
Morton

(10) Patent No.: US 10,901,112 B2
(45) Date of Patent: *Jan. 26, 2021

(54) X-RAY SCANNING SYSTEM WITH STATIONARY X-RAY SOURCES

(71) Applicant: Rapiscan Systems, Inc., Torrance, CA (US)

(72) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/192,112

(22) Filed: Nov. 15, 2018

(65) Prior Publication Data

US 2019/0353821 A1    Nov. 21, 2019

Related U.S. Application Data

(63) Continuation of application No. 15/439,837, filed on Feb. 22, 2017, now Pat. No. 10,175,381, which is a
(Continued)

(30) Foreign Application Priority Data

Apr. 25, 2003 (GB) .................................. 0309371.3
Apr. 25, 2003 (GB) .................................. 0309383.8
(Continued)

(51) Int. Cl.
*G01V 5/00* (2006.01)
*A61B 6/03* (2006.01)
(Continued)

(52) U.S. Cl.
CPC ............ *G01V 5/0016* (2013.01); *A61B 6/032* (2013.01); *A61B 6/4014* (2013.01);
(Continued)

(58) Field of Classification Search
CPC ...... G01V 5/0016; G01V 5/005; A61B 6/032; A61B 6/035; A61B 6/4014; A61B 6/4488;
(Continued)

(56) References Cited

U.S. PATENT DOCUMENTS 768,538 A    8/1904  McElroy
2,005,180 A    6/1935  Cronin
(Continued)

FOREIGN PATENT DOCUMENTS

AT          392160 B       2/1991
AU       2003254124 A1    2/2004
(Continued)

OTHER PUBLICATIONS

US 5,987,079 A, 11/1999, Scott (withdrawn)
(Continued)

*Primary Examiner* — Courtney D Thomas
(74) *Attorney, Agent, or Firm* — Novel IP

(57) ABSTRACT

The present application discloses an X-ray scanner having an X-ray source arranged to emit X-rays from source points through an imaging volume. The scanner may further include an array of X-ray detectors which may be arranged around the imaging volume and may be arranged to output detector signals in response to the detection of X-rays. The scanner may further include a conveyor arranged to convey an object through the imaging volume in a scan direction, and may also include at least one processor arranged to process the detector signals to produce an image data set defining an image of the object. The image may have a resolution in the scan direction that is at least 90% as high as in one direction, and in some cases two directions, orthogonal to the scan direction.

68 Claims, 13 Drawing Sheets

Related U.S. Application Data continuation of application No. 14/641,777, filed on Mar. 9, 2015, now Pat. No. 9,618,648, which is a continuation of application No. 13/548,873, filed on Jul. 13, 2012, now Pat. No. 9,020,095, which is a continuation of application No. 12/712,476, filed on Feb. 25, 2010, now Pat. No. 8,243,876, which is a continuation-in-part of application No. 12/485,897, filed on Jun. 16, 2009, now abandoned, which is a continuation of application No. 10/554,656, filed as application No. PCT/GB2004/001729 on Apr. 23, 2004, now Pat. No. 7,564,939, said application No. 12/712,476 is a continuation-in-part of application No. 12/371,853, filed on Feb. 16, 2009, now Pat. No. 7,903,789, which is a continuation of application No. 10/554,975, filed as application No. PCT/GB2004/001741 on Apr. 23, 2004, now Pat. No. 7,512,215, said application No. 12/712,476 is a continuation-in-part of application No. 12/651,479, filed on Jan. 3, 2010, now abandoned, which is a continuation of application No. 10/554,654, filed as application No. PCT/GB2004/001731 on Apr. 23, 2004, now Pat. No. 7,664,230, said application No. 12/712,476 is a continuation-in-part of application No. 12/364,067, filed on Feb. 2, 2009, now abandoned, which is a continuation of application No. 12/033,035, filed on Feb. 19, 2008, now Pat. No. 7,505,563, which is a continuation of application No. 10/554,569, filed as application No. PCT/GB2004/001732 on Apr. 23, 2004, now Pat. No. 7,349,525, said application No. 12/712,476 is a continuation-in-part of application No. 12/211,219, filed on Sep. 16, 2008, now Pat. No. 7,724,868, which is a continuation of application No. 10/554,655, filed as application No. PCT/GB2004/001751 on Apr. 23, 2004, now Pat. No. 7,440,543, said application No. 12/712,476 is a continuation-in-part of application No. 10/554,570, filed as application No. PCT/GB2004/001747 on Apr. 23, 2004, now Pat. No. 7,684,538, said application No. 12/712,476 is a continuation-in-part of application No. 12/097,422, filed as application No. PCT/GB2006/004684 on Dec. 15, 2006, now Pat. No. 7,876,879.

(60) Provisional application No. 61/155,572, filed on Feb. 26, 2009.

(30) Foreign Application Priority Data

| | | |
|---|---|---|
| Apr. 25, 2003 | (GB) | 0309387.9 |
| Dec. 16, 2005 | (GB) | 0525593.0 |
| Feb. 25, 2009 | (GB) | 0903198.0 |

(51) Int. Cl.
 *A61B 6/00* (2006.01)
 *G01N 23/046* (2018.01)
 *H05G 1/70* (2006.01)

(52) U.S. Cl.
 CPC ......... *A61B 6/4488* (2013.01); *G01N 23/046* (2013.01); *G01V 5/005* (2013.01); *H05G 1/70* (2013.01); *G01N 2223/419* (2013.01)

(58) Field of Classification Search
 CPC ... H05G 1/70; G01N 23/046; G01N 2223/419
 USPC .......................................................... 378/57
 See application file for complete search history.

(56) References Cited

U.S. PATENT DOCUMENTS

| | | |
|---|---|---|
| 2,006,291 A | 6/1935 | Barrows |
| 2,007,003 A | 7/1935 | Shy |
| 2,009,060 A | 7/1935 | Hiers |
| 2,010,020 A | 8/1935 | Hans |
| 2,010,278 A | 8/1935 | Snyder |
| 2,101,143 A | 12/1937 | Laidig |
| 2,299,251 A | 10/1942 | Perbal |
| 2,333,525 A | 11/1943 | Cox |
| 2,831,123 A | 4/1958 | Daly |
| 2,842,694 A | 7/1958 | Rolf |
| 2,952,790 A | 9/1960 | Steen |
| 2,999,935 A | 9/1961 | Foster |
| 3,138,729 A | 6/1964 | Henke |
| 3,143,651 A | 8/1964 | Riccardo |
| 3,239,706 A | 3/1966 | Farrell |
| 3,610,994 A | 10/1971 | Sheldon |
| 3,707,672 A | 12/1972 | Miller |
| 3,713,156 A | 1/1973 | Pothier |
| 3,766,387 A | 10/1973 | Heffan |
| 3,768,645 A | 10/1973 | Conway |
| 3,780,291 A | 12/1973 | Stein |
| 3,784,837 A | 1/1974 | Holmstrom |
| 3,790,785 A | 2/1974 | Paolini |
| 3,790,799 A | 2/1974 | Stein |
| 3,848,130 A | 11/1974 | Macovski |
| 3,854,049 A | 12/1974 | Mistretta |
| 3,867,637 A | 2/1975 | Braun |
| RE28,544 E | 9/1975 | Stein |
| 3,965,358 A | 6/1976 | Macovski |
| 3,980,889 A | 9/1976 | Haas |
| 4,031,401 A | 6/1977 | Jacob |
| 4,031,545 A | 6/1977 | Stein |
| 4,045,672 A | 8/1977 | Watanabe |
| 4,047,035 A | 9/1977 | Dennhoven |
| 4,057,725 A | 11/1977 | Wagner |
| 4,064,411 A | 12/1977 | Iwasaki |
| 4,105,922 A | 8/1978 | Lambert |
| 4,122,783 A | 10/1978 | Pretini |
| 4,139,771 A | 2/1979 | Dennhoven |
| 4,158,770 A | 6/1979 | Davis, Jr. |
| 4,165,472 A | 8/1979 | Wittry |
| 4,171,254 A | 10/1979 | Koenecke |
| 4,185,205 A | 1/1980 | Ballas |
| 4,200,800 A | 4/1980 | Swift |
| 4,210,811 A | 7/1980 | Dennhoven |
| 4,216,499 A | 8/1980 | Dennhoven |
| 4,228,353 A | 10/1980 | Johnson |
| 4,228,357 A | 10/1980 | Annis |
| 4,238,706 A | 12/1980 | Hayasaka |
| 4,241,404 A | 12/1980 | Lux |
| 4,242,583 A | 12/1980 | Annis |
| 4,245,158 A | 1/1981 | Burstein |
| 4,259,721 A | 3/1981 | Kuznia |
| 4,260,898 A | 4/1981 | Annis |
| 4,266,425 A | 5/1981 | Allport |
| 4,274,005 A | 6/1981 | Yamamura |
| 4,297,580 A | 10/1981 | Juner |
| 4,303,860 A | 12/1981 | Bjorkholm |
| 4,309,637 A | 1/1982 | Fetter |
| 4,340,816 A | 7/1982 | Schott |
| 4,342,914 A | 8/1982 | Bjorkholm |
| 4,344,011 A | 8/1982 | Hayashi |
| 4,352,021 A | 9/1982 | Boyd |
| 4,352,196 A | 9/1982 | Gabbay |
| 4,366,382 A | 12/1982 | Kotowski |
| 4,366,576 A | 12/1982 | Annis |
| 4,375,695 A | 3/1983 | Harding |
| 4,384,209 A | 5/1983 | Wagner |
| 4,389,729 A | 6/1983 | Stein |
| 4,399,403 A | 8/1983 | Strandberg, Jr. |
| 4,405,876 A | 9/1983 | Iversen |
| 4,414,682 A | 11/1983 | Annis |
| 4,420,382 A | 12/1983 | Riedl |
| 4,422,177 A | 12/1983 | Mastronardi |
| 4,430,568 A | 2/1984 | Yoshida |

(56) References Cited

U.S. PATENT DOCUMENTS

| | | |
|---|---|---|
| 4,461,020 A | 7/1984 | Huebner |
| 4,468,802 A | 8/1984 | Friedel |
| 4,471,343 A | 9/1984 | Lemelson |
| 4,472,822 A | 9/1984 | Swift |
| 4,511,799 A | 4/1985 | Bjorkholm |
| 4,531,226 A | 7/1985 | Peschmann |
| 4,566,113 A | 1/1986 | Doenges |
| 4,571,491 A | 2/1986 | Vinegar |
| 4,593,355 A | 6/1986 | Chase |
| 4,599,740 A | 7/1986 | Cable |
| 4,622,687 A | 11/1986 | Whitaker |
| 4,622,688 A | 11/1986 | Diemer |
| 4,625,324 A | 11/1986 | Blaskis |
| 4,641,330 A | 2/1987 | Herwig |
| 4,670,895 A | 6/1987 | Penato |
| 4,672,649 A | 6/1987 | Rutt |
| 4,675,890 A | 6/1987 | Plessis |
| 4,677,651 A | 6/1987 | Hartl |
| 4,691,332 A | 9/1987 | Burstein |
| 4,719,645 A | 1/1988 | Yamabe |
| 4,736,400 A | 4/1988 | Koller |
| 4,736,401 A | 4/1988 | Donges |
| 4,754,469 A | 6/1988 | Harding |
| 4,763,345 A | 8/1988 | Barbaric |
| 4,768,214 A | 8/1988 | Bjorkholm |
| 4,788,704 A | 11/1988 | Donges |
| 4,788,706 A | 11/1988 | Jacobson |
| 4,789,930 A | 12/1988 | Sones |
| 4,799,247 A | 1/1989 | Annis |
| 4,809,312 A | 2/1989 | Annis |
| 4,825,454 A | 4/1989 | Annis |
| RE32,961 E | 6/1989 | Wagner |
| 4,845,731 A | 7/1989 | Vidmar |
| 4,845,769 A | 7/1989 | Burstein |
| 4,852,131 A | 7/1989 | Armistead |
| 4,866,745 A | 9/1989 | Akai |
| 4,868,856 A | 9/1989 | Frith |
| 4,884,289 A * | 11/1989 | Glockmann ......... G01N 23/043 378/57 |
| 4,887,604 A | 12/1989 | Shefer |
| 4,893,015 A | 1/1990 | Kubierschky |
| 4,894,775 A | 1/1990 | Kritchman |
| 4,899,283 A | 2/1990 | Annis |
| 4,928,296 A | 5/1990 | Kadambi |
| 4,945,562 A | 7/1990 | Staub |
| 4,956,856 A | 9/1990 | Harding |
| 4,958,363 A | 9/1990 | Nelson |
| 4,963,746 A | 10/1990 | Morgan |
| 4,975,968 A | 12/1990 | Yukl |
| 4,979,202 A | 12/1990 | Siczek |
| 4,987,584 A | 1/1991 | Doenges |
| 4,991,189 A | 2/1991 | Boomgaarden |
| 4,991,194 A | 2/1991 | Laurent |
| 5,007,072 A | 4/1991 | Jenkins |
| 5,008,911 A | 4/1991 | Harding |
| 5,018,181 A | 5/1991 | Iversen |
| 5,022,062 A | 6/1991 | Annis |
| 5,033,106 A | 7/1991 | Kita |
| 5,056,124 A | 10/1991 | Kakimoto |
| 5,056,127 A | 10/1991 | Iversen |
| 5,065,418 A | 11/1991 | Bermbach |
| 5,068,882 A | 11/1991 | Eberhard |
| 5,073,910 A | 12/1991 | Eberhard |
| 5,081,456 A | 1/1992 | Michiguchi |
| 5,091,924 A | 2/1992 | Bermbach |
| 5,091,927 A | 2/1992 | Golitzer |
| 5,098,640 A | 3/1992 | Gozani |
| 5,105,452 A | 4/1992 | McInerney |
| 5,127,030 A | 6/1992 | Annis |
| 5,138,308 A | 8/1992 | Clerc |
| 5,144,191 A | 9/1992 | Jones |
| 5,155,365 A | 10/1992 | Cann |
| 5,159,234 A | 10/1992 | Wegmann |
| 5,172,401 A | 12/1992 | Asari |
| 5,179,581 A | 1/1993 | Annis |
| 5,181,234 A | 1/1993 | Smith |
| 5,182,764 A | 1/1993 | Peschmann |
| 5,191,600 A | 3/1993 | Vincent |
| 5,195,112 A | 3/1993 | Vincent |
| 5,224,144 A | 6/1993 | Annis |
| 5,227,800 A | 7/1993 | Huguenin |
| 5,237,598 A | 8/1993 | Albert |
| 5,247,556 A | 9/1993 | Eckert |
| 5,247,561 A | 9/1993 | Kotowski |
| 5,253,283 A | 10/1993 | Annis |
| 5,259,014 A | 11/1993 | Brettschneider |
| 5,263,075 A | 11/1993 | McGann |
| 5,265,144 A | 11/1993 | Harding |
| 5,268,955 A | 12/1993 | Burke |
| 5,272,627 A | 12/1993 | Maschhoff |
| 5,305,363 A | 4/1994 | Burke |
| 5,313,511 A | 5/1994 | Annis |
| 5,319,547 A | 6/1994 | Krug |
| 5,329,180 A | 7/1994 | Popli |
| 5,339,080 A | 8/1994 | Steinway |
| 5,345,240 A | 9/1994 | Frazier |
| 5,365,567 A | 11/1994 | Ohtsuchi |
| 5,367,552 A | 11/1994 | Peschmann |
| 5,375,156 A | 12/1994 | Kuo-Petravic |
| 5,379,334 A | 1/1995 | Zimmer |
| 5,410,156 A | 4/1995 | Miller |
| 5,412,702 A | 5/1995 | Sata |
| 5,414,622 A | 5/1995 | Walters |
| 5,420,905 A | 5/1995 | Bertozzi |
| 5,428,657 A | 6/1995 | Papanicolopoulos |
| 5,467,377 A | 11/1995 | Dawson |
| 5,481,584 A | 1/1996 | Tang |
| 5,490,196 A | 2/1996 | Rudich |
| 5,490,218 A | 2/1996 | Krug |
| 5,493,596 A | 2/1996 | Annis |
| 5,511,104 A | 4/1996 | Mueller |
| 5,515,414 A | 5/1996 | D Achard Van Enschut |
| 5,524,133 A | 6/1996 | Neale |
| 5,541,975 A | 7/1996 | Anderson |
| 5,552,705 A | 9/1996 | Keller |
| 5,557,108 A | 9/1996 | Tumer |
| 5,557,283 A | 9/1996 | Sheen |
| 5,568,829 A | 10/1996 | Crawford |
| 5,570,403 A | 10/1996 | Yamazaki |
| 5,596,621 A | 1/1997 | Schwarz |
| 5,600,303 A | 2/1997 | Husseiny |
| 5,600,700 A | 2/1997 | Krug |
| 5,604,778 A | 2/1997 | Polacin |
| 5,606,167 A | 2/1997 | Miller |
| 5,616,926 A | 4/1997 | Shinada |
| 5,633,906 A | 5/1997 | Hell |
| 5,633,907 A | 5/1997 | Gravelle |
| 5,638,420 A | 6/1997 | Armistead |
| 5,642,393 A | 6/1997 | Krug |
| 5,642,394 A | 6/1997 | Rothschild |
| 5,648,997 A | 7/1997 | Chao |
| 5,651,047 A | 7/1997 | Moorman |
| 5,654,995 A | 8/1997 | Flohr |
| 5,661,774 A | 8/1997 | Gordon |
| 5,666,393 A | 9/1997 | Annis |
| 5,680,432 A | 10/1997 | Voss |
| 5,687,210 A | 11/1997 | Maitrejean |
| 5,689,239 A | 11/1997 | Turner |
| 5,689,541 A | 11/1997 | Schardt |
| 5,692,028 A | 11/1997 | Geus |
| 5,712,889 A | 1/1998 | Lanzara |
| 5,712,926 A | 1/1998 | Eberhard |
| 5,745,543 A | 4/1998 | De Bokx |
| 5,751,837 A | 5/1998 | Watanabe |
| 5,764,683 A | 6/1998 | Swift |
| 5,768,334 A | 6/1998 | Maitrejean |
| 5,787,145 A | 7/1998 | Geus |
| 5,796,802 A | 8/1998 | Gordon |
| 5,798,972 A | 8/1998 | Lao |
| 5,805,660 A | 9/1998 | Perion |
| 5,812,630 A | 9/1998 | Blaffert |
| 5,818,897 A | 10/1998 | Gordon |
| 5,838,758 A | 11/1998 | Krug |
| 5,838,759 A | 11/1998 | Armistead |

(56) References Cited

U.S. PATENT DOCUMENTS

| | | |
|---|---|---|
| 5,841,831 A | 11/1998 | Hell |
| 5,841,832 A | 11/1998 | Mazess |
| 5,859,891 A | 1/1999 | Hibbard |
| 5,864,146 A | 1/1999 | Karellas |
| 5,879,807 A | 3/1999 | Inoue |
| 5,881,122 A | 3/1999 | Crawford |
| 5,887,047 A | 3/1999 | Bailey |
| 5,889,833 A | 3/1999 | Silver |
| 5,901,198 A | 5/1999 | Crawford |
| 5,903,623 A | 5/1999 | Swift |
| 5,905,806 A | 5/1999 | Eberhard |
| 5,907,593 A | 5/1999 | Hsieh |
| 5,909,477 A | 6/1999 | Crawford |
| 5,910,973 A | 6/1999 | Grodzins |
| 5,930,326 A | 7/1999 | Rothschild |
| 5,940,468 A | 8/1999 | Huang |
| 5,943,388 A | 8/1999 | Tuemer |
| 5,966,422 A | 10/1999 | Dafni |
| 5,974,111 A | 10/1999 | Krug |
| 5,982,843 A | 11/1999 | Bailey |
| 5,987,097 A | 11/1999 | Salasoo |
| 6,014,419 A | 1/2000 | Hu |
| 6,018,562 A | 1/2000 | Willson |
| 6,021,174 A | 2/2000 | Campbell |
| 6,026,135 A | 2/2000 | McFee |
| 6,026,143 A | 2/2000 | Simanovsky |
| 6,026,171 A | 2/2000 | Hiraoglu |
| 6,031,890 A | 2/2000 | Bermbach |
| 6,035,014 A | 3/2000 | Hiraoglu |
| 6,037,597 A | 3/2000 | Karavolos |
| 6,054,712 A | 4/2000 | Komardin |
| 6,058,158 A | 5/2000 | Eiler |
| 6,067,344 A | 5/2000 | Grodzins |
| 6,067,366 A | 5/2000 | Simanovsky |
| 6,075,836 A | 6/2000 | Ning |
| 6,075,871 A | 6/2000 | Simanovsky |
| 6,076,400 A | 6/2000 | Bechwati |
| 6,078,642 A | 6/2000 | Simanovsky |
| 6,081,580 A | 6/2000 | Grodzins |
| 6,088,423 A | 7/2000 | Krug |
| 6,088,426 A | 7/2000 | Miller |
| 6,091,795 A | 7/2000 | Schafer |
| 6,094,472 A | 7/2000 | Smith |
| 6,108,396 A | 8/2000 | Bechwati |
| 6,108,575 A | 8/2000 | Besson |
| 6,111,974 A | 8/2000 | Hiraoglu |
| 6,118,850 A | 9/2000 | Mayo |
| 6,118,852 A | 9/2000 | Rogers |
| 6,122,343 A | 9/2000 | Pidcock |
| 6,125,167 A | 9/2000 | Morgan |
| 6,128,365 A | 10/2000 | Bechwati |
| 6,130,502 A | 10/2000 | Kobayashi |
| 6,149,592 A | 11/2000 | Yanof |
| 6,151,381 A | 11/2000 | Grodzins |
| 6,163,591 A | 12/2000 | Benjamin |
| 6,181,765 B1 | 1/2001 | Sribar |
| 6,183,139 B1 | 2/2001 | Solomon |
| 6,184,841 B1 | 2/2001 | Shober |
| 6,185,272 B1 | 2/2001 | Hiraoglu |
| 6,188,743 B1 | 2/2001 | Tybinkowski |
| 6,188,745 B1 | 2/2001 | Gordon |
| 6,188,747 B1 | 2/2001 | Geus |
| 6,192,101 B1 | 2/2001 | Grodzins |
| 6,192,104 B1 | 2/2001 | Adams |
| 6,195,413 B1 | 2/2001 | Geus |
| 6,195,444 B1 | 2/2001 | Simanovsky |
| 6,198,795 B1 | 3/2001 | Naumann |
| 6,216,540 B1 | 4/2001 | Nelson |
| 6,218,943 B1 | 4/2001 | Ellenbogen |
| 6,229,870 B1 | 5/2001 | Morgan |
| 6,236,709 B1 | 5/2001 | Perry |
| 6,240,157 B1 | 5/2001 | Danielsson |
| 6,249,567 B1 | 6/2001 | Rothschild |
| 6,252,929 B1 | 6/2001 | Swift |
| 6,252,932 B1 | 6/2001 | Arakawa |
| 6,256,369 B1 | 7/2001 | Lai |
| 6,256,404 B1 | 7/2001 | Gordon |
| 6,269,142 B1 | 7/2001 | Smith |
| 6,272,230 B1 | 8/2001 | Hiraoglu |
| 6,278,115 B1 | 8/2001 | Annis |
| 6,282,260 B1 | 8/2001 | Grodzins |
| 6,288,676 B1 | 9/2001 | Maloney |
| 6,292,533 B1 | 9/2001 | Swift |
| 6,298,110 B1 | 10/2001 | Ning |
| 6,301,326 B2 | 10/2001 | Bjorkholm |
| 6,304,629 B1 | 10/2001 | Conway |
| 6,317,509 B1 | 11/2001 | Simanovsky |
| 6,320,933 B1 | 11/2001 | Grodzins |
| 6,324,243 B1 | 11/2001 | Edic |
| 6,324,249 B1 | 11/2001 | Fazzio |
| 6,332,015 B1 | 12/2001 | Honda |
| 6,341,154 B1 | 1/2002 | Besson |
| 6,342,696 B1 | 1/2002 | Chadwick |
| 6,345,113 B1 | 2/2002 | Crawford |
| 6,347,132 B1 | 2/2002 | Annis |
| 6,356,620 B1 | 3/2002 | Rothschild |
| 6,359,582 B1 | 3/2002 | MacAleese |
| 6,385,292 B1 | 5/2002 | Dunham |
| 6,404,230 B1 | 6/2002 | Cairns |
| 6,417,797 B1 | 7/2002 | Cousins |
| 6,418,189 B1 | 7/2002 | Schafer |
| 6,421,420 B1 | 7/2002 | Grodzins |
| 6,424,695 B1 | 7/2002 | Grodzins |
| 6,429,578 B1 | 8/2002 | Danielsson |
| 6,430,255 B2 | 8/2002 | Fenkart |
| 6,430,260 B1 | 8/2002 | Snyder |
| 6,434,219 B1 | 8/2002 | Rothschild |
| 6,435,715 B1 | 8/2002 | Betz |
| 6,438,201 B1 | 8/2002 | Mazess |
| 6,442,233 B1 | 8/2002 | Grodzins |
| 6,445,765 B1 | 9/2002 | Frank |
| 6,449,331 B1 | 9/2002 | Nutt |
| 6,449,337 B1 | 9/2002 | Honda |
| 6,453,003 B1 | 9/2002 | Springer |
| 6,453,007 B2 | 9/2002 | Adams |
| 6,456,093 B1 | 9/2002 | Merkel |
| 6,456,684 B1 | 9/2002 | Mun |
| 6,459,755 B1 | 10/2002 | Li |
| 6,459,761 B1 | 10/2002 | Grodzins |
| 6,459,764 B1 | 10/2002 | Chalmers |
| 6,469,624 B1 | 10/2002 | Whan |
| 6,470,065 B1 | 10/2002 | Lauther |
| 6,473,487 B1 | 10/2002 | Le |
| RE37,899 E | 11/2002 | Grodzins |
| 6,480,141 B1 | 11/2002 | Toth |
| 6,480,571 B1 | 11/2002 | Andrews |
| 6,483,894 B2 | 11/2002 | Hartick |
| 6,501,414 B2 | 12/2002 | Arndt |
| 6,507,025 B1 | 1/2003 | Verbinski |
| 6,532,276 B1 | 3/2003 | Hartick |
| 6,542,574 B2 | 4/2003 | Grodzins |
| 6,542,578 B2 | 4/2003 | Ries |
| 6,542,580 B1 | 4/2003 | Carver |
| 6,546,072 B1 | 4/2003 | Chalmers |
| 6,552,346 B2 | 4/2003 | Verbinski |
| 6,553,096 B1 | 4/2003 | Zhou |
| 6,556,653 B2 | 4/2003 | Hussein |
| 6,563,903 B2 | 5/2003 | Kang |
| 6,563,906 B2 | 5/2003 | Hussein |
| 6,580,778 B2 | 6/2003 | Meder |
| 6,580,780 B1 | 6/2003 | Miller |
| 6,584,170 B2 | 6/2003 | Aust |
| 6,590,956 B2 | 7/2003 | Fenkart |
| 6,597,760 B2 | 7/2003 | Beneke |
| 6,606,516 B2 | 8/2003 | Levine |
| 6,618,466 B1 | 9/2003 | Ning |
| 6,621,888 B2 | 9/2003 | Grodzins |
| 6,624,425 B2 | 9/2003 | Nisius |
| 6,628,745 B1 | 9/2003 | Annis |
| 6,636,581 B2 | 10/2003 | Sorenson |
| 6,642,513 B1 | 11/2003 | Jenkins |
| 6,647,091 B2 | 11/2003 | Fenkart |
| 6,647,094 B2 | 11/2003 | Harding |
| 6,647,095 B2 | 11/2003 | Hsieh |

(56) References Cited

U.S. PATENT DOCUMENTS

| | | |
|---|---|---|
| 6,650,276 B2 | 11/2003 | Lawless |
| 6,653,588 B1 | 11/2003 | Gillard-Hickman |
| 6,654,440 B1 | 11/2003 | Hsieh |
| 6,658,087 B2 | 12/2003 | Chalmers |
| 6,661,866 B1 | 12/2003 | Limkeman |
| 6,663,280 B2 | 12/2003 | Doenges |
| 6,665,373 B1 | 12/2003 | Kotowski |
| 6,665,433 B2 | 12/2003 | Roder |
| 6,674,838 B1 | 1/2004 | Barrett |
| 6,687,333 B2 | 2/2004 | Carroll |
| 6,690,766 B2 | 2/2004 | Kresse |
| 6,707,879 B2 | 3/2004 | McClelland |
| 6,715,533 B2 | 4/2004 | Kresse |
| 6,721,387 B1 | 4/2004 | Naidu |
| 6,735,271 B1 | 5/2004 | Rand |
| 6,737,652 B2 | 5/2004 | Lanza |
| 6,748,043 B1 | 6/2004 | Dobbs |
| 6,751,293 B1 | 6/2004 | Barrett |
| 6,754,298 B2 | 6/2004 | Fessler |
| 6,760,407 B2 | 7/2004 | Price |
| 6,763,635 B1 | 7/2004 | Lowman |
| 6,768,317 B2 | 7/2004 | Moeller |
| 6,770,884 B2 | 8/2004 | Bryman |
| 6,775,348 B2 | 8/2004 | Hoffman |
| 6,785,357 B2 | 8/2004 | Bernardi |
| 6,785,359 B2 | 8/2004 | Lemaitre |
| 6,788,761 B2 | 9/2004 | Bijjani |
| 6,798,863 B2 | 9/2004 | Sato |
| 6,807,248 B2 | 10/2004 | Mihara |
| 6,812,426 B1 | 11/2004 | Kotowski |
| 6,813,374 B1 | 11/2004 | Karimi |
| 6,815,670 B2 | 11/2004 | Jenkins |
| 6,816,571 B2 | 11/2004 | Bijjani |
| 6,819,742 B1 | 11/2004 | Miller |
| 6,827,265 B2 | 12/2004 | Knowles |
| 6,830,185 B2 | 12/2004 | Tsikos |
| 6,831,590 B1 | 12/2004 | Steinway |
| 6,837,422 B1 | 1/2005 | Meder |
| 6,837,432 B2 | 1/2005 | Tsikos |
| 6,839,403 B1 | 1/2005 | Kotowski |
| 6,840,122 B1 | 1/2005 | Jenkins |
| 6,843,599 B2 | 1/2005 | Le |
| 6,856,271 B1 | 2/2005 | Hausner |
| 6,856,667 B2 | 2/2005 | Ellenbogen |
| 6,859,514 B2 | 2/2005 | Hoffman |
| 6,876,322 B2 | 4/2005 | Keller |
| 6,891,381 B2 | 5/2005 | Bailey |
| 6,894,636 B2 | 5/2005 | Anderton |
| 6,901,135 B2 | 5/2005 | Fox |
| 6,906,329 B2 | 6/2005 | Bryman |
| 6,907,101 B2 | 6/2005 | Hoffman |
| 6,920,196 B2 | 7/2005 | Ueno |
| 6,920,197 B2 | 7/2005 | Kang |
| 6,922,455 B2 | 7/2005 | Jurczyk |
| 6,922,460 B2 | 7/2005 | Skatter |
| 6,922,461 B2 | 7/2005 | Kang |
| 6,928,141 B2 | 8/2005 | Carver |
| 6,933,504 B2 | 8/2005 | Hoffman |
| 6,934,354 B2 | 8/2005 | Hoffman |
| 6,940,071 B2 | 9/2005 | Ramsden |
| 6,944,264 B2 | 9/2005 | Bijjani |
| 6,947,517 B2 | 9/2005 | Hoffman |
| 6,950,492 B2 | 9/2005 | Besson |
| 6,950,493 B2 | 9/2005 | Besson |
| 6,952,163 B2 | 10/2005 | Huey |
| 6,953,935 B1 | 10/2005 | Hoffman |
| 6,957,913 B2 | 10/2005 | Renkart |
| 6,962,289 B2 | 11/2005 | Vatan |
| 6,968,030 B2 | 11/2005 | Hoffman |
| 6,968,034 B2 | 11/2005 | Ellenbogen |
| 6,971,577 B2 | 12/2005 | Tsikos |
| 6,973,158 B2 | 12/2005 | Besson |
| 6,975,698 B2 | 12/2005 | Katcha |
| 6,975,703 B2 | 12/2005 | Wilson |
| 6,978,936 B2 | 12/2005 | Tsikos |
| 6,980,627 B2 | 12/2005 | Qiu |
| 6,990,171 B2 | 1/2006 | Toth |
| 6,990,172 B2 | 1/2006 | Toth |
| 6,991,371 B2 | 1/2006 | Georgeson |
| 6,993,115 B2 | 1/2006 | McGuire |
| 6,996,209 B2 | 2/2006 | Marek |
| 7,010,083 B2 | 3/2006 | Hoffman |
| 7,010,094 B2 | 3/2006 | Grodzins |
| 7,012,256 B1 | 3/2006 | Roos |
| 7,012,989 B2 | 3/2006 | Holland |
| 7,016,459 B2 | 3/2006 | Ellenbogen |
| 7,020,232 B2 | 3/2006 | Rand |
| 7,020,241 B2 | 3/2006 | Beneke |
| 7,020,242 B2 | 3/2006 | Ellenbogen |
| 7,023,950 B1 | 4/2006 | Annis |
| 7,023,956 B2 | 4/2006 | Heaton |
| 7,023,957 B2 | 4/2006 | Bijjani |
| 7,027,553 B2 | 4/2006 | Dunham |
| 7,027,554 B2 | 4/2006 | Gaultier |
| 7,031,430 B2 | 4/2006 | Kaucic, Jr. |
| 7,031,434 B1 | 4/2006 | Saunders |
| 7,034,313 B2 | 4/2006 | Hoffman |
| 7,039,154 B1 | 5/2006 | Ellenbogen |
| 7,039,159 B2 | 5/2006 | Muenchau |
| 7,045,787 B1 | 5/2006 | Verbinski |
| 7,046,756 B2 | 5/2006 | Hoffman |
| 7,046,761 B2 | 5/2006 | Ellenbogen |
| 7,050,529 B2 | 5/2006 | Hoffman |
| 7,050,536 B1 | 5/2006 | Fenkart |
| 7,050,540 B2 | 5/2006 | Wilkins |
| 7,054,408 B2 | 5/2006 | Jiang |
| 7,062,009 B2 | 6/2006 | Karimi |
| 7,062,011 B1 | 6/2006 | Tybinkowski |
| 7,062,074 B1 | 6/2006 | Beneke |
| 7,064,334 B2 | 6/2006 | Hoffman |
| 7,065,175 B2 | 6/2006 | Green |
| 7,065,179 B2 | 6/2006 | Block |
| 7,068,749 B2 | 6/2006 | Kollegal |
| 7,068,750 B2 | 6/2006 | Toth |
| 7,068,751 B2 | 6/2006 | Toth |
| 7,072,434 B1 | 7/2006 | Tybinkowski |
| 7,076,029 B2 | 7/2006 | Toth |
| 7,078,699 B2 | 7/2006 | Seppi |
| 7,079,624 B1 | 7/2006 | Miller |
| 7,081,628 B2 | 7/2006 | Granfors |
| 7,084,404 B2 | 8/2006 | Hoffman |
| 7,087,902 B2 | 8/2006 | Wang |
| 7,088,799 B2 | 8/2006 | Hoffman |
| 7,090,133 B2 | 8/2006 | Zhu |
| 7,092,481 B2 | 8/2006 | Hoffman |
| 7,092,485 B2 | 8/2006 | Kravis |
| 7,099,434 B2 | 8/2006 | Adams |
| 7,103,137 B2 | 9/2006 | Seppi |
| 7,106,830 B2 | 9/2006 | Rosner |
| 7,110,488 B2 | 9/2006 | Katcha |
| 7,110,493 B1 | 9/2006 | Kotowski |
| 7,112,797 B2 | 9/2006 | Hoge |
| 7,116,749 B2 | 10/2006 | Besson |
| 7,116,751 B2 | 10/2006 | Ellenbogen |
| 7,119,553 B2 | 10/2006 | Yang |
| 7,120,222 B2 | 10/2006 | Hoffman |
| 7,123,681 B2 | 10/2006 | Ellenbogen |
| 7,127,027 B2 | 10/2006 | Hoffman |
| 7,130,374 B1 | 10/2006 | Jacobs |
| RE39,396 E | 11/2006 | Swift |
| 7,133,491 B2 | 11/2006 | Bernardi |
| 7,136,450 B2 | 11/2006 | Ying |
| 7,136,451 B2 | 11/2006 | Naidu |
| 7,139,367 B1 | 11/2006 | Le |
| 7,139,406 B2 | 11/2006 | McClelland |
| 7,142,629 B2 | 11/2006 | Edic |
| 7,149,278 B2 | 12/2006 | Arenson |
| 7,149,339 B2 | 12/2006 | Veneruso |
| 7,155,812 B1 | 1/2007 | Peterson |
| 7,158,611 B2 | 1/2007 | Heismann |
| 7,164,747 B2 | 1/2007 | Ellenbogen |
| 7,164,750 B2 | 1/2007 | Nabors |
| 7,166,458 B2 | 1/2007 | Ballerstadt |
| 7,167,539 B1 | 1/2007 | Hoffman |

(56) References Cited

U.S. PATENT DOCUMENTS

| | | |
|---|---|---|
| 7,173,998 B2 | 2/2007 | Hoffman |
| 7,177,387 B2 | 2/2007 | Yasunaga |
| 7,177,391 B2 | 2/2007 | Chapin |
| 7,183,906 B2 | 2/2007 | Zanovitch |
| 7,184,520 B1 | 2/2007 | Sano |
| 7,184,814 B2 | 2/2007 | Lang |
| 7,187,756 B2 | 3/2007 | Gohno |
| 7,190,757 B2 | 3/2007 | Ying |
| 7,192,031 B2 | 3/2007 | Dunham |
| 7,197,113 B1 | 3/2007 | Katcha |
| 7,197,116 B2 | 3/2007 | Dunham |
| 7,197,172 B1 | 3/2007 | Naidu |
| 7,203,269 B2 | 4/2007 | Huber |
| 7,203,271 B2 | 4/2007 | Benz |
| 7,203,282 B2 | 4/2007 | Brauss |
| 7,203,629 B2 | 4/2007 | Oezis |
| 7,206,379 B2 | 4/2007 | Lemaitre |
| 7,207,713 B2 | 4/2007 | Lowman |
| 7,215,731 B1 | 5/2007 | Basu |
| 7,215,738 B2 | 5/2007 | Muenchau |
| 7,218,700 B2 | 5/2007 | Huber |
| 7,218,704 B1 | 5/2007 | Adams |
| 7,224,763 B2 | 5/2007 | Naidu |
| 7,224,765 B2 | 5/2007 | Ellenbogen |
| 7,224,766 B2 | 5/2007 | Jiang |
| 7,224,769 B2 | 5/2007 | Turner |
| 7,233,640 B2 | 6/2007 | Ikhlef |
| 7,233,644 B1 | 6/2007 | Bendahan |
| 7,236,564 B2 | 6/2007 | Hopkins |
| 7,238,945 B2 | 7/2007 | Hoffman |
| 7,247,856 B2 | 7/2007 | Hoge |
| 7,248,673 B2 | 7/2007 | Miller |
| 7,251,310 B2 | 7/2007 | Smith |
| 7,253,727 B2 | 8/2007 | Jenkins |
| 7,260,170 B2 | 8/2007 | Arenson |
| 7,260,171 B1 | 8/2007 | Arenson |
| 7,260,172 B2 | 8/2007 | Arenson |
| 7,260,173 B2 | 8/2007 | Wakayama |
| 7,260,174 B2 | 8/2007 | Hoffman |
| 7,260,182 B2 | 8/2007 | Toth |
| 7,261,466 B2 | 8/2007 | Bhatt |
| 7,263,160 B2 | 8/2007 | Schlomka |
| 7,266,180 B1 | 9/2007 | Saunders |
| 7,272,429 B2 | 9/2007 | Walker |
| 7,274,767 B2 | 9/2007 | Clayton |
| 7,277,577 B2 | 10/2007 | Ying |
| 7,279,120 B2 | 10/2007 | Cheng |
| 7,280,631 B2 | 10/2007 | De Man |
| 7,282,727 B2 | 10/2007 | Retsky |
| 7,283,604 B2 | 10/2007 | De Man |
| 7,283,609 B2 | 10/2007 | Possin |
| 7,295,019 B2 | 11/2007 | Yang |
| 7,295,651 B2 | 11/2007 | Delgado |
| 7,295,691 B2 | 11/2007 | Uppaluri |
| 7,298,812 B2 | 11/2007 | Tkaczyk |
| 7,302,083 B2 | 11/2007 | Larson |
| 7,308,073 B2 | 12/2007 | Tkaczyk |
| 7,308,074 B2 | 12/2007 | Jiang |
| 7,308,077 B2 | 12/2007 | Bijjani |
| 7,317,195 B2 | 1/2008 | Eikman |
| 7,317,390 B2 | 1/2008 | Huey |
| 7,319,737 B2 | 1/2008 | Singh |
| 7,322,745 B2 | 1/2008 | Agrawal |
| 7,324,625 B2 | 1/2008 | Eilbert |
| 7,327,853 B2 | 2/2008 | Ying |
| 7,330,527 B2 | 2/2008 | Hoffman |
| 7,330,535 B2 | 2/2008 | Arenson |
| 7,333,587 B2 | 2/2008 | De Man |
| 7,333,588 B2 | 2/2008 | Mistretta |
| 7,333,589 B2 | 2/2008 | Ellenbogen |
| 7,335,887 B1 | 2/2008 | Verbinski |
| 7,336,769 B2 | 2/2008 | Arenson |
| 7,340,525 B1 | 3/2008 | Bhatia |
| 7,349,525 B2 | 3/2008 | Morton |
| 7,354,197 B2 | 4/2008 | Bhatt |
| 7,366,280 B2 | 4/2008 | Lounsberry |
| 7,366,282 B2 | 4/2008 | Peschmann |
| 7,369,640 B2 | 5/2008 | Seppi |
| 7,369,643 B2 | 5/2008 | Kotowski |
| 7,372,934 B2 | 5/2008 | De Man |
| 7,376,218 B2 | 5/2008 | Chapin |
| 7,400,701 B1 | 7/2008 | Cason |
| 7,412,026 B2 | 8/2008 | Liu |
| 7,417,440 B2 | 8/2008 | Peschmann |
| 7,418,073 B2 | 8/2008 | Schlomka |
| 7,426,260 B2 | 9/2008 | Cantu |
| 7,440,543 B2 | 10/2008 | Morton |
| 7,466,799 B2 | 12/2008 | Miller |
| 7,483,510 B2 | 1/2009 | Carver |
| 7,486,760 B2 | 2/2009 | Harding |
| 7,486,768 B2 | 2/2009 | Allman |
| 7,486,769 B2 | 2/2009 | Brondo, Jr. |
| 7,490,984 B2 | 2/2009 | Bhatt |
| 7,492,855 B2 | 2/2009 | Hopkins |
| 7,505,563 B2 | 3/2009 | Morton |
| 7,508,916 B2 | 3/2009 | Frontera |
| 7,510,324 B2 | 3/2009 | Bhatt |
| 7,512,215 B2 | 3/2009 | Morton |
| 7,551,714 B2 | 6/2009 | Rothschild |
| 7,551,718 B2 | 6/2009 | Rothschild |
| 7,555,099 B2 | 6/2009 | Rothschild |
| 7,564,939 B2 | 7/2009 | Morton |
| 7,565,939 B2 | 7/2009 | Ando |
| 7,579,845 B2 | 8/2009 | Peschmann |
| 7,590,215 B2 | 9/2009 | Schlomka |
| 7,593,506 B2 | 9/2009 | Cason |
| 7,596,275 B1 | 9/2009 | Richardson |
| 7,636,638 B2 | 12/2009 | Russ |
| 7,643,866 B2 | 1/2010 | Heismann |
| 7,649,981 B2 | 1/2010 | Seppi |
| 7,664,230 B2 | 2/2010 | Morton |
| 7,684,538 B2 | 3/2010 | Morton |
| 7,697,665 B2 | 4/2010 | Yonezawa |
| 7,724,868 B2 | 5/2010 | Morton |
| 7,728,397 B2 | 6/2010 | Gorrell |
| 7,734,066 B2 | 6/2010 | Delia |
| 7,738,632 B2 | 6/2010 | Popescu |
| 7,769,132 B1 | 8/2010 | Hurd |
| 7,778,382 B2 | 8/2010 | Hoffman |
| 7,796,795 B2 | 9/2010 | Uppaluri |
| 7,835,495 B2 | 11/2010 | Harding |
| 7,856,081 B2 | 12/2010 | Peschmann |
| 7,864,920 B2 | 1/2011 | Rothschild |
| 7,876,879 B2 | 1/2011 | Morton |
| 7,885,372 B2 | 2/2011 | Edic |
| 7,903,789 B2 | 3/2011 | Morton |
| 7,924,979 B2 | 4/2011 | Rothschild |
| 7,929,663 B2 | 4/2011 | Morton |
| 7,949,101 B2 | 5/2011 | Morton |
| 7,970,096 B2 | 6/2011 | Pavlovich |
| 7,978,816 B2 | 7/2011 | Matsuura |
| 7,995,707 B2 | 8/2011 | Rothschild |
| 8,039,812 B1 | 10/2011 | Crocker |
| 8,085,897 B2 | 12/2011 | Morton |
| 8,094,784 B2 | 1/2012 | Morton |
| 8,111,803 B2 | 2/2012 | Edic |
| 8,135,110 B2 | 3/2012 | Morton |
| 8,138,770 B2 | 3/2012 | Peschmann |
| 8,204,173 B2 | 6/2012 | Betcke |
| 8,223,919 B2 | 7/2012 | Morton |
| 8,243,876 B2 * | 8/2012 | Morton ............... A61B 6/4014 378/19 |
| 8,311,313 B1 | 11/2012 | Gamble |
| 8,331,535 B2 | 12/2012 | Morton |
| 8,428,217 B2 | 4/2013 | Peschmann |
| 8,451,974 B2 | 5/2013 | Morton |
| 8,552,722 B2 | 10/2013 | Lionheart |
| 8,559,592 B2 | 10/2013 | Betcke |
| 8,625,735 B2 | 1/2014 | Morton |
| 8,654,924 B2 | 2/2014 | Behling |
| 8,804,899 B2 | 8/2014 | Morton |
| 8,824,637 B2 | 9/2014 | Morton |
| 8,837,669 B2 | 9/2014 | Morton |
| 8,842,808 B2 | 9/2014 | Rothschild |

(56) References Cited

U.S. PATENT DOCUMENTS

| | | |
|---|---|---|
| 8,885,794 B2 | 11/2014 | Morton |
| 8,958,526 B2 | 2/2015 | Morton |
| 8,971,484 B2 | 3/2015 | Beckmann |
| 9,001,973 B2 | 4/2015 | Morton |
| 9,020,095 B2 | 4/2015 | Morton |
| 9,042,511 B2 | 5/2015 | Peschmann |
| 9,046,465 B2 | 6/2015 | Thompson |
| 9,048,061 B2 | 6/2015 | Morton |
| 9,086,497 B2 | 7/2015 | Bendahan |
| 9,093,187 B1 | 7/2015 | Johnson |
| 9,093,245 B2 | 7/2015 | Morton |
| 9,113,839 B2 | 8/2015 | Morton |
| 9,158,030 B2 | 10/2015 | Morton |
| 9,183,647 B2 | 11/2015 | Morton |
| 9,208,988 B2 | 12/2015 | Morton |
| 9,263,225 B2 | 2/2016 | Morton |
| 9,286,686 B2 | 3/2016 | Lang |
| 9,420,677 B2 | 8/2016 | Morton |
| 9,442,082 B2 | 9/2016 | Morton |
| 9,442,213 B2 | 9/2016 | Bendahan |
| 9,562,866 B2 | 2/2017 | Morton |
| 9,576,766 B2 | 2/2017 | Morton |
| 9,606,259 B2 | 3/2017 | Morton |
| 9,618,648 B2 | 4/2017 | Morton |
| 9,638,646 B2 | 5/2017 | Morton |
| 9,675,306 B2 | 6/2017 | Morton |
| 9,714,920 B2 | 7/2017 | Lionheart |
| 9,726,619 B2 | 8/2017 | Thompson |
| 9,747,705 B2 | 8/2017 | Morton |
| 9,915,752 B2 | 3/2018 | Peschmann |
| 10,107,783 B2 | 10/2018 | Lionheart |
| 10,175,381 B2 | 1/2019 | Morton |
| 10,295,483 B2 | 5/2019 | Morton |
| 10,591,424 B2 | 3/2020 | Morton |
| 2001/0022346 A1 | 9/2001 | Katagami |
| 2001/0022830 A1 | 9/2001 | Sommer |
| 2001/0033635 A1 | 10/2001 | Kuwabara |
| 2001/0050972 A1 | 12/2001 | Yamada |
| 2002/0008655 A1 | 1/2002 | Haj-Yousef |
| 2002/0031202 A1 | 3/2002 | Callerame |
| 2002/0082492 A1 | 6/2002 | Grzeszczuk |
| 2002/0085674 A1 | 7/2002 | Price |
| 2002/0094064 A1 | 7/2002 | Zhou |
| 2002/0094117 A1 | 7/2002 | Funahashi |
| 2002/0097836 A1 | 7/2002 | Grodzins |
| 2002/0101958 A1 | 8/2002 | Bertsche |
| 2002/0126798 A1 | 9/2002 | Harris |
| 2002/0140336 A1 | 10/2002 | Stoner |
| 2002/0176531 A1 | 11/2002 | McClelland |
| 2002/0177770 A1 | 11/2002 | Lang |
| 2003/0009202 A1 | 1/2003 | Levine |
| 2003/0021377 A1 | 1/2003 | Turner |
| 2003/0023592 A1 | 1/2003 | Modica |
| 2003/0031352 A1 | 2/2003 | Nelson |
| 2003/0043957 A1 | 3/2003 | Pelc |
| 2003/0048868 A1 | 3/2003 | Bailey |
| 2003/0053597 A1 | 3/2003 | Flohr |
| 2003/0072407 A1 | 4/2003 | Mihara |
| 2003/0076921 A1 | 4/2003 | Mihara |
| 2003/0076924 A1 | 4/2003 | Mario |
| 2003/0081720 A1* | 5/2003 | Swift .................. G21K 5/10 378/41 |
| 2003/0085163 A1 | 5/2003 | Chan |
| 2003/0091148 A1 | 5/2003 | Bittner |
| 2003/0108155 A1 | 6/2003 | Wilkins |
| 2003/0179126 A1 | 9/2003 | Jablonski |
| 2003/0190011 A1 | 10/2003 | Beneke |
| 2003/0215120 A1 | 11/2003 | Uppaluri |
| 2003/0216644 A1 | 11/2003 | Hall |
| 2004/0016271 A1 | 1/2004 | Shah |
| 2004/0017224 A1 | 1/2004 | Tumer |
| 2004/0017887 A1 | 1/2004 | Le |
| 2004/0017888 A1 | 1/2004 | Seppi |
| 2004/0021623 A1 | 2/2004 | Nicolas |
| 2004/0022292 A1 | 2/2004 | Morton |
| 2004/0057554 A1 | 3/2004 | Bjorkholm |
| 2004/0066879 A1 | 4/2004 | Machida |
| 2004/0077943 A1 | 4/2004 | Meaney |
| 2004/0081270 A1 | 4/2004 | Heuscher |
| 2004/0094064 A1 | 5/2004 | Taguchi |
| 2004/0094707 A1 | 5/2004 | Jenkins |
| 2004/0096030 A1 | 5/2004 | Banchieri |
| 2004/0101098 A1 | 5/2004 | Bijjani |
| 2004/0109532 A1 | 6/2004 | Ford |
| 2004/0120454 A1 | 6/2004 | Ellenbogen |
| 2004/0141584 A1 | 7/2004 | Bernardi |
| 2004/0202282 A1 | 10/2004 | Miller |
| 2004/0213378 A1 | 10/2004 | Zhou |
| 2004/0213379 A1 | 10/2004 | Bittl |
| 2004/0223585 A1 | 11/2004 | Heismann |
| 2004/0232054 A1 | 11/2004 | Brown |
| 2004/0234023 A1 | 11/2004 | Kollegal |
| 2004/0245449 A1 | 12/2004 | Nakashige |
| 2004/0252807 A1 | 12/2004 | Skatter |
| 2004/0258198 A1 | 12/2004 | Carver |
| 2004/0258305 A1 | 12/2004 | Burnham |
| 2005/0002492 A1 | 1/2005 | Rother |
| 2005/0008073 A1 | 1/2005 | Techmer |
| 2005/0031075 A1 | 2/2005 | Hopkins |
| 2005/0053189 A1 | 3/2005 | Gohno |
| 2005/0057354 A1 | 3/2005 | Jenkins |
| 2005/0058242 A1 | 3/2005 | Peschmann |
| 2005/0082491 A1 | 4/2005 | Seppi |
| 2005/0084069 A1 | 4/2005 | Du |
| 2005/0084073 A1 | 4/2005 | Seppi |
| 2005/0089140 A1 | 4/2005 | Mario |
| 2005/0100126 A1 | 5/2005 | Mistretta |
| 2005/0100135 A1 | 5/2005 | Lowman |
| 2005/0104603 A1 | 5/2005 | Peschmann |
| 2005/0105665 A1 | 5/2005 | Grodzins |
| 2005/0105682 A1 | 5/2005 | Heumann |
| 2005/0111610 A1 | 5/2005 | De Man |
| 2005/0111619 A1 | 5/2005 | Bijjani |
| 2005/0117683 A1 | 6/2005 | Mishin |
| 2005/0117700 A1 | 6/2005 | Peschmann |
| 2005/0123092 A1 | 6/2005 | Mistretta |
| 2005/0140603 A1 | 6/2005 | Kim |
| 2005/0157842 A1 | 7/2005 | Agrawal |
| 2005/0157925 A1 | 7/2005 | Lorenz |
| 2005/0169422 A1 | 8/2005 | Ellenbogen |
| 2005/0169423 A1 | 8/2005 | Ellenbogen |
| 2005/0175151 A1 | 8/2005 | Dunham |
| 2005/0180542 A1 | 8/2005 | Leue |
| 2005/0190882 A1 | 9/2005 | McGuire |
| 2005/0226364 A1 | 10/2005 | Bernard De Man |
| 2005/0238232 A1 | 10/2005 | Ying |
| 2005/0249416 A1 | 11/2005 | Leue |
| 2005/0276377 A1 | 12/2005 | Carol |
| 2005/0276382 A1 | 12/2005 | Lesiak |
| 2005/0281390 A1 | 12/2005 | Johnson |
| 2006/0002585 A1 | 1/2006 | Larson |
| 2006/0008047 A1 | 1/2006 | Zhou |
| 2006/0018428 A1 | 1/2006 | Li |
| 2006/0050842 A1 | 3/2006 | Wang |
| 2006/0056584 A1 | 3/2006 | Allman |
| 2006/0098773 A1 | 5/2006 | Peschmann |
| 2006/0109949 A1 | 5/2006 | Tkaczyk |
| 2006/0109954 A1 | 5/2006 | Gohno |
| 2006/0113163 A1 | 6/2006 | Hu |
| 2006/0133571 A1 | 6/2006 | Winsor |
| 2006/0134000 A1 | 6/2006 | Heismann |
| 2006/0140341 A1 | 6/2006 | Carver |
| 2006/0145771 A1 | 7/2006 | Strange |
| 2006/0203961 A1 | 9/2006 | Morton |
| 2006/0233295 A1 | 10/2006 | Edic |
| 2006/0233297 A1 | 10/2006 | Ishiyama |
| 2006/0256924 A1 | 11/2006 | Morton |
| 2006/0273259 A1 | 12/2006 | Li |
| 2006/0280286 A1 | 12/2006 | Kaval |
| 2006/0291623 A1 | 12/2006 | Smith |
| 2007/0003003 A1 | 1/2007 | Seppi |
| 2007/0025512 A1 | 2/2007 | Gertsenshteyn |
| 2007/0053495 A1 | 3/2007 | Morton |
| 2007/0064873 A1 | 3/2007 | Gabioud |

(56) References Cited

U.S. PATENT DOCUMENTS

| | | |
|---|---|---|
| 2007/0096030 A1 | 5/2007 | Li |
| 2007/0110215 A1 | 5/2007 | Hu |
| 2007/0122003 A1 | 5/2007 | Dobkin |
| 2007/0133740 A1 | 6/2007 | Kang |
| 2007/0172023 A1 | 7/2007 | Morton |
| 2007/0172024 A1 | 7/2007 | Morton |
| 2007/0183568 A1 | 8/2007 | Kang |
| 2007/0183575 A1 | 8/2007 | Lemaitre |
| 2007/0189597 A1 | 8/2007 | Limer |
| 2007/0203430 A1 | 8/2007 | Lang |
| 2007/0205367 A1 | 9/2007 | Deman |
| 2007/0237288 A1 | 10/2007 | Tkaczyk |
| 2007/0242802 A1 | 10/2007 | Dafni |
| 2007/0263767 A1 | 11/2007 | Brondo |
| 2007/0269005 A1 | 11/2007 | Chalmers |
| 2007/0297570 A1 | 12/2007 | Kerpershoek |
| 2008/0019483 A1 | 1/2008 | Andrews |
| 2008/0031507 A1 | 2/2008 | Uppaluri |
| 2008/0043912 A1 | 2/2008 | Harding |
| 2008/0043920 A1 | 2/2008 | Liu |
| 2008/0056432 A1 | 3/2008 | Pack |
| 2008/0056435 A1 | 3/2008 | Basu |
| 2008/0056436 A1 | 3/2008 | Pack |
| 2008/0056437 A1 | 3/2008 | Pack |
| 2008/0056444 A1 | 3/2008 | Skatter |
| 2008/0069420 A1 | 3/2008 | Zhang |
| 2008/0112540 A1 | 5/2008 | Rogers |
| 2008/0123803 A1 | 5/2008 | De Man |
| 2008/0130974 A1 | 6/2008 | Xu |
| 2008/0144774 A1 | 6/2008 | Mortor |
| 2008/0198967 A1 | 8/2008 | Connelly |
| 2008/0213803 A1 | 9/2008 | Cowley |
| 2008/0237480 A1 | 10/2008 | Robinson |
| 2008/0267355 A1 | 10/2008 | Morton |
| 2008/0304622 A1 | 12/2008 | Morton |
| 2009/0003514 A1 | 1/2009 | Edic |
| 2009/0010386 A1 | 1/2009 | Peschmann |
| 2009/0022264 A1 | 1/2009 | Zhou |
| 2009/0034792 A1 | 2/2009 | Kennison |
| 2009/0041186 A1 | 2/2009 | Gray |
| 2009/0060135 A1 | 3/2009 | Morton |
| 2009/0086898 A1 | 4/2009 | Richardson |
| 2009/0097836 A1 | 4/2009 | Tanaka |
| 2009/0110259 A1 | 4/2009 | Yin |
| 2009/0147910 A1 | 6/2009 | Edic |
| 2009/0159451 A1 | 6/2009 | Tomantschger |
| 2009/0161816 A1 | 6/2009 | De Man |
| 2009/0168958 A1 | 7/2009 | Cozzini |
| 2009/0185660 A1 | 7/2009 | Zou |
| 2009/0207967 A1 | 8/2009 | Liu |
| 2009/0213989 A1 | 8/2009 | Harding |
| 2009/0265386 A1 | 10/2009 | March |
| 2009/0274277 A1 | 11/2009 | Morton |
| 2009/0316855 A1 | 12/2009 | Morton |
| 2010/0020920 A1 | 1/2010 | Mertelmeier |
| 2010/0020934 A1 | 1/2010 | Morton |
| 2010/0046716 A1 | 2/2010 | Freudenberger |
| 2010/0098219 A1 | 4/2010 | Vermilyea |
| 2010/0111265 A1 | 5/2010 | Holm |
| 2010/0172476 A1 | 7/2010 | Morton |
| 2010/0220835 A1 | 9/2010 | Gibson |
| 2010/0246754 A1 | 9/2010 | Morton |
| 2010/0284509 A1 | 11/2010 | Oreper |
| 2010/0316192 A1 | 12/2010 | Hauttmann |
| 2010/0329532 A1 | 12/2010 | Masuda |
| 2011/0007876 A1 | 1/2011 | Morton |
| 2011/0170757 A1 | 7/2011 | Pan |
| 2011/0188725 A1 | 8/2011 | Yu |
| 2011/0222662 A1 | 9/2011 | Behling |
| 2011/0228899 A1 | 9/2011 | Funk |
| 2011/0243382 A1 | 10/2011 | Morton |
| 2011/0243413 A1 | 10/2011 | Tkaczyk |
| 2011/0249788 A1 | 10/2011 | Joachim |
| 2012/0219116 A1 | 8/2012 | Thompson |
| 2013/0156161 A1 | 6/2013 | Andrews |
| 2013/0195253 A1 | 8/2013 | Andrews |
| 2013/0251098 A1 | 9/2013 | Morton |
| 2013/0264483 A1 | 10/2013 | Abenaim |
| 2014/0023181 A1 | 1/2014 | Noshi |
| 2014/0185754 A1* | 7/2014 | Tang ................ G01V 5/005 |
| | | 378/57 |
| 2014/0211916 A1 | 7/2014 | Morton |
| 2014/0294147 A1 | 10/2014 | Chen |
| 2014/0342631 A1 | 11/2014 | Morton |
| 2015/0357148 A1 | 12/2015 | Morton |
| 2016/0343533 A1 | 11/2016 | Morton |
| 2017/0161922 A1 | 6/2017 | Morton |
| 2018/0038988 A1 | 2/2018 | Morton |
| 2018/0128754 A1 | 5/2018 | Thompson |
| 2019/0178821 A1 | 6/2019 | Morton |
| 2019/0353821 A1 | 11/2019 | Morton |
| 2020/0103357 A1 | 4/2020 | Morton |
| 2020/0200690 A1 | 6/2020 | Morton |

FOREIGN PATENT DOCUMENTS

| | | |
|---|---|---|
| CA | 2365045 | 6/2003 |
| CN | 85107860 A | 10/1986 |
| CN | 1050769 | 4/1991 |
| CN | 1130498 A | 9/1996 |
| CN | 1194718 | 9/1998 |
| CN | 1309768 | 8/2001 |
| CN | 1316827 | 10/2001 |
| CN | 1550215 A | 12/2004 |
| CN | 1626039 A | 6/2005 |
| CN | 1708256 A | 12/2005 |
| CN | 1745296 A | 3/2006 |
| CN | 1780585 A | 5/2006 |
| CN | 1795527 A | 6/2006 |
| CN | 100371689 C | 7/2006 |
| CN | 1820705 A | 8/2006 |
| CN | 1937961 A | 3/2007 |
| CN | 101048802 | 10/2007 |
| CN | 201034948 | 3/2008 |
| CN | 101185577 | 5/2008 |
| CN | 101189534 A | 5/2008 |
| CN | 101303317 A | 11/2008 |
| CN | 101512379 | 8/2009 |
| CN | 101842052 | 9/2010 |
| DE | 2729353 A1 | 1/1979 |
| DE | 3638378 | 5/1988 |
| DE | 3840398 A1 | 6/1989 |
| DE | 4410757 A1 | 1/1995 |
| DE | 4432205 C1 | 1/1996 |
| DE | 4425691 A1 | 2/1996 |
| DE | 4436688 A1 | 4/1996 |
| DE | 19745998 A1 | 3/1999 |
| DE | 10036210 A1 | 11/2001 |
| DE | 10319547 | 11/2004 |
| DE | 10319549 B3 | 12/2004 |
| DE | 102004056590 A1 | 6/2005 |
| DE | 102005048389 A1 | 4/2007 |
| EP | 0115125 A1 | 8/1984 |
| EP | 0142249 A2 | 5/1985 |
| EP | 0198276 A1 | 10/1986 |
| EP | 0424912 A2 | 5/1991 |
| EP | 0432568 | 6/1991 |
| EP | 0531993 A1 | 3/1993 |
| EP | 0564292 | 10/1993 |
| EP | 0584871 A1 | 3/1994 |
| EP | 0795919 A2 | 9/1997 |
| EP | 0873511 A1 | 10/1998 |
| EP | 0924742 A2 | 6/1999 |
| EP | 0930046 A2 | 7/1999 |
| EP | 1063538 | 12/2000 |
| EP | 1277439 A1 | 1/2003 |
| EP | 1298055 A2 | 4/2003 |
| EP | 1371970 A2 | 12/2003 |
| EP | 1374776 A1 | 1/2004 |
| EP | 1540318 A1 | 6/2005 |
| EP | 1558142 A1 | 8/2005 |
| EP | 1617764 B1 | 1/2006 |
| EP | 1618368 B1 | 1/2006 |
| EP | 1618584 A2 | 1/2006 |

(56) References Cited

FOREIGN PATENT DOCUMENTS

| | | |
|---|---|---|
| EP | 1620875 A2 | 2/2006 |
| EP | 1689640 A2 | 8/2006 |
| EP | 1969356 | 9/2008 |
| EP | 2002789 B1 | 12/2008 |
| EP | 2017605 A1 | 1/2009 |
| EP | 1618585 B1 | 6/2009 |
| EP | 2151681 B1 | 2/2010 |
| EP | 1739413 | 5/2010 |
| EP | 1618584 B1 | 9/2011 |
| EP | 2406809 | 1/2012 |
| EP | 2435955 A4 | 4/2012 |
| EP | 2436013 | 4/2012 |
| EP | 2278606 B1 | 10/2013 |
| EP | 2287882 B1 | 10/2013 |
| EP | 2267750 B1 | 11/2013 |
| EP | 2678668 | 1/2014 |
| EP | 1970700 | 7/2014 |
| EP | 2854644 | 4/2015 |
| EP | 3267361 A1 | 1/2018 |
| EP | 3282393 A1 | 2/2018 |
| EP | 1618353 B1 | 2/2019 |
| FR | 2328280 A1 | 5/1977 |
| FR | 2675629 A1 | 10/1992 |
| GB | 1149796 A | 4/1969 |
| GB | 1272498 A | 4/1972 |
| GB | 1497396 A | 1/1978 |
| GB | 1526041 A | 9/1978 |
| GB | 2015245 A | 9/1979 |
| GB | 2089109 A | 6/1982 |
| GB | 2133208 | 7/1984 |
| GB | 2212903 A | 8/1989 |
| GB | 2212975 A | 8/1989 |
| GB | 2244900 | 12/1991 |
| GB | 2329817 A | 3/1995 |
| GB | 2285506 A | 7/1995 |
| GB | 2299251 | 9/1996 |
| GB | 2356453 A | 5/2001 |
| GB | 2360405 | 9/2001 |
| GB | 2360405 A | 9/2001 |
| GB | 2414072 A | 11/2005 |
| GB | 2416655 A | 2/2006 |
| GB | 2416944 A | 2/2006 |
| GB | 2417821 A | 3/2006 |
| GB | 2418529 A | 3/2006 |
| GB | 2423687 A | 8/2006 |
| GB | 2437777 A | 11/2007 |
| GB | 2471421 A | 12/2010 |
| JP | 50012990 | 2/1975 |
| JP | 50081080 A | 7/1975 |
| JP | S51055286 | 5/1976 |
| JP | S51078696 | 7/1976 |
| JP | S52050186 | 4/1977 |
| JP | S52124890 | 10/1977 |
| JP | S5427793 | 3/1979 |
| JP | S5493993 | 7/1979 |
| JP | S55046408 | 4/1980 |
| JP | 56086448 | 7/1981 |
| JP | S56167464 | 12/1981 |
| JP | S5717524 A | 1/1982 |
| JP | S57110854 | 7/1982 |
| JP | 570175247 | 10/1982 |
| JP | S57175247 A | 10/1982 |
| JP | 58212045 A | 12/1983 |
| JP | 590016254 | 1/1984 |
| JP | S591625 A | 1/1984 |
| JP | S5916254 A | 1/1984 |
| JP | 59075549 | 4/1984 |
| JP | S5975549 A | 4/1984 |
| JP | 59174744 | 10/1984 |
| JP | 600015546 | 1/1985 |
| JP | S601554 A | 1/1985 |
| JP | 600021440 | 2/1985 |
| JP | S56038957 A | 2/1985 |
| JP | S60021440 | 2/1985 |
| JP | 60073442 A | 4/1985 |
| JP | S60181851 | 12/1985 |
| JP | S61028039 | 2/1986 |
| JP | 61107642 | 5/1986 |
| JP | S6104193 | 10/1986 |
| JP | 62044940 A | 2/1987 |
| JP | 62064977 | 3/1987 |
| JP | S62121773 | 8/1987 |
| JP | 63016535 | 1/1988 |
| JP | S63150840 | 6/1988 |
| JP | 64034333 A | 2/1989 |
| JP | S6486938 | 3/1989 |
| JP | 1296544 A | 11/1989 |
| JP | 03198975 A1 | 8/1991 |
| JP | H0479128 A | 3/1992 |
| JP | H04319237 | 11/1992 |
| JP | 05100037 A | 4/1993 |
| JP | H05135721 A | 6/1993 |
| JP | H05182617 A | 7/1993 |
| JP | 05192327 A | 8/1993 |
| JP | H05060381 | 9/1993 |
| JP | H05290768 A | 11/1993 |
| JP | 5325851 | 12/1993 |
| JP | H05325851 | 12/1993 |
| JP | 060038957 | 2/1994 |
| JP | H0638957 A | 2/1994 |
| JP | H06133960 | 5/1994 |
| JP | 06162974 | 6/1994 |
| JP | H06169911 | 6/1994 |
| JP | H06261895 | 9/1994 |
| JP | 6296607 | 10/1994 |
| JP | H07012756 | 1/1995 |
| JP | H07057113 | 3/1995 |
| JP | H07093525 | 4/1995 |
| JP | H08178872 | 7/1996 |
| JP | H08299322 | 11/1996 |
| JP | 1138743 A | 12/1996 |
| JP | H09171788 | 6/1997 |
| JP | 10005206 A | 1/1998 |
| JP | H10001209 | 1/1998 |
| JP | 1172952 A | 2/1998 |
| JP | 10075944 A | 3/1998 |
| JP | 1998075944 A | 3/1998 |
| JP | 10506195 | 6/1998 |
| JP | H10211196 A | 8/1998 |
| JP | H10272128 | 10/1998 |
| JP | H11500229 | 1/1999 |
| JP | 11146871 A | 6/1999 |
| JP | H11230918 | 8/1999 |
| JP | H11230918 A | 8/1999 |
| JP | 11262486 A | 9/1999 |
| JP | H11273597 | 10/1999 |
| JP | 2000107173 A | 4/2000 |
| JP | 2000175895 | 6/2000 |
| JP | 200113089 | 1/2001 |
| JP | 2001023557 | 1/2001 |
| JP | 2001502473 | 2/2001 |
| JP | 2001083171 | 3/2001 |
| JP | 2001176408 A | 6/2001 |
| JP | 2001204723 | 7/2001 |
| JP | 2001233440 | 8/2001 |
| JP | 2001351551 | 12/2001 |
| JP | 2002039966 | 2/2002 |
| JP | 2002503816 | 2/2002 |
| JP | 2002162472 | 6/2002 |
| JP | 2002168805 | 6/2002 |
| JP | 2002195961 | 7/2002 |
| JP | 2002257751 | 9/2002 |
| JP | 2002535625 | 10/2002 |
| JP | 2002320610 A | 11/2002 |
| JP | 2002343291 | 11/2002 |
| JP | 2002370814 | 12/2002 |
| JP | 2003092076 | 3/2003 |
| JP | 2003121392 | 4/2003 |
| JP | 2003126075 A | 5/2003 |
| JP | 2003135442 | 5/2003 |
| JP | 2003257347 | 9/2003 |
| JP | 2004000605 A | 1/2004 |
| JP | 2004079128 A | 3/2004 |
| JP | 2004226253 | 8/2004 |

(56) References Cited

FOREIGN PATENT DOCUMENTS

| | | |
|---|---|---|
| JP | 2004233206 | 8/2004 |
| JP | 2004311245 | 11/2004 |
| JP | 2004347328 | 12/2004 |
| JP | 2004357724 | 12/2004 |
| JP | 2005013768 A | 1/2005 |
| JP | 2005110722 | 4/2005 |
| JP | 2005177469 A | 7/2005 |
| JP | 2005534009 | 11/2005 |
| JP | 2005534009 A | 11/2005 |
| JP | 2006502386 | 1/2006 |
| JP | 2006071514 | 3/2006 |
| JP | 2006128137 | 5/2006 |
| JP | 2006167463 | 6/2006 |
| JP | 2006518039 | 8/2006 |
| JP | 2006320464 | 11/2006 |
| JP | 2006524809 A | 11/2006 |
| JP | 2006351272 A | 12/2006 |
| JP | 2007010455 | 1/2007 |
| JP | 2007500357 A | 1/2007 |
| JP | 2007508561 A | 4/2007 |
| JP | 2007265981 | 10/2007 |
| JP | 2007533993 A | 11/2007 |
| JP | 2008113960 | 5/2008 |
| JP | 2008166059 A | 7/2008 |
| JP | 2008178714 | 8/2008 |
| JP | 2008212840 | 9/2008 |
| JP | 2008268035 | 11/2008 |
| JP | 3147024 | 12/2008 |
| JP | 2009083632 | 4/2009 |
| JP | 2009519457 | 5/2009 |
| JP | 2010060572 | 3/2010 |
| JP | 100211196 | 9/2010 |
| NL | 1021026 | 1/2004 |
| NL | 1027596 C2 | 11/2005 |
| SU | 1022236 A1 | 6/1983 |
| WO | 1997018462 A1 | 5/1992 |
| WO | 9217771 A1 | 10/1992 |
| WO | 1992017771 A1 | 10/1992 |
| WO | 9528715 A2 | 10/1995 |
| WO | 9718462 A | 5/1997 |
| WO | 9718462 A1 | 5/1997 |
| WO | 1997018462 A1 | 5/1997 |
| WO | 1998002763 A1 | 1/1998 |
| WO | 9941676 | 8/1999 |
| WO | 199950882 | 10/1999 |
| WO | 1999050882 | 10/1999 |
| WO | 9960387 A2 | 11/1999 |
| WO | 0231857 A1 | 4/2002 |
| WO | 200231857 | 4/2002 |
| WO | 2002031857 | 4/2002 |
| WO | 2002031857 A1 | 4/2002 |
| WO | 2003029844 | 4/2003 |
| WO | 03042674 | 5/2003 |
| WO | 03051201 A2 | 6/2003 |
| WO | 2003051201 | 6/2003 |
| WO | 2003051201 A2 | 6/2003 |
| WO | 2003052397 | 6/2003 |
| WO | 2003065772 | 8/2003 |
| WO | 2003088302 | 10/2003 |
| WO | 03105159 | 12/2003 |
| WO | 2004008968 A1 | 1/2004 |
| WO | 2004008970 A1 | 1/2004 |
| WO | 2004010127 | 1/2004 |
| WO | 2004010127 A1 | 1/2004 |
| WO | 2004010381 A1 | 1/2004 |
| WO | 2004031755 | 4/2004 |
| WO | 2004031755 A2 | 4/2004 |
| WO | 2004037088 | 5/2004 |
| WO | 2004042769 A1 | 5/2004 |
| WO | 2004054329 A2 | 6/2004 |
| WO | 2004072685 | 8/2004 |
| WO | 02004096050 | 11/2004 |
| WO | 2004096050 | 11/2004 |
| WO | 2004097344 | 11/2004 |
| WO | 2004097344 A2 | 11/2004 |
| WO | 2004097386 | 11/2004 |
| WO | 2004097386 A1 | 11/2004 |
| WO | 2004097886 A2 | 11/2004 |
| WO | 2004097888 | 11/2004 |
| WO | 2004097888 A2 | 11/2004 |
| WO | 2004097889 | 11/2004 |
| WO | 2004097889 A2 | 11/2004 |
| WO | 2004105610 A | 12/2004 |
| WO | 2004111625 | 12/2004 |
| WO | 2004097886 | 1/2005 |
| WO | 2005017566 A2 | 2/2005 |
| WO | 2005037074 | 4/2005 |
| WO | 2005050256 | 6/2005 |
| WO | 2005050405 A2 | 6/2005 |
| WO | 2005084351 | 9/2005 |
| WO | 2005095931 | 10/2005 |
| WO | 2005102170 | 11/2005 |
| WO | 2006027122 A1 | 3/2006 |
| WO | 2006047718 | 5/2006 |
| WO | 2006069708 | 7/2006 |
| WO | 2006069708 A1 | 7/2006 |
| WO | 2006074431 A2 | 7/2006 |
| WO | 2006130630 | 12/2006 |
| WO | 2006130630 A2 | 12/2006 |
| WO | 2006137919 | 12/2006 |
| WO | 2006135586 | 2/2007 |
| WO | 2007051418 | 5/2007 |
| WO | 2007068933 | 6/2007 |
| WO | 2007068933 A1 | 6/2007 |
| WO | 2007076707 | 7/2007 |
| WO | 2007079675 | 7/2007 |
| WO | 2008018021 | 2/2008 |
| WO | 2008024825 A2 | 2/2008 |
| WO | 2008027703 A2 | 3/2008 |
| WO | 2008034232 A1 | 3/2008 |
| WO | 2008068691 | 6/2008 |
| WO | 2008094305 | 8/2008 |
| WO | 2008115275 | 9/2008 |
| WO | 2008118568 | 10/2008 |
| WO | 2008118568 A2 | 10/2008 |
| WO | 2009005932 | 1/2009 |
| WO | 2009006044 | 1/2009 |
| WO | 2009012453 | 1/2009 |
| WO | 2009012453 A1 | 1/2009 |
| WO | 2009024817 | 2/2009 |
| WO | 2009025935 | 2/2009 |
| WO | 2009130491 | 10/2009 |
| WO | 2010007375 A2 | 1/2010 |
| WO | 2010086653 | 8/2010 |
| WO | 2010097621 A2 | 9/2010 |
| WO | 2010138574 | 12/2010 |
| WO | 2010138607 | 12/2010 |
| WO | 2010138607 A1 | 12/2010 |
| WO | 2010141659 A1 | 12/2010 |
| WO | 2010145016 A1 | 12/2010 |
| WO | 2012115629 A1 | 8/2012 |
| WO | 20012115629 A1 | 8/2012 |
| WO | 2013184103 A1 | 12/2013 |

OTHER PUBLICATIONS

Development of ultra-fast X-ray computed tomography scanner system, INS 98-43 6068772 A9823-8760J-016 (PHA); B9812-7510B-113 (EEA) NDN-174-0606-8771-7, Hori, K.; Fujimoto, T.; Kawanishi, K., Editor--Nalcioglu, O., Abbreviated Journal Title--1997 IEEE Nuclear Science Symposium, Conference Record (Cat. No. 97CH36135), Part No. vol. 2, 1997, pp. 1003-1008 vol. 2, 2 vol. xlviii+1761 page(s), ISBN-0 7803 4258 5.

Sheen, David et al. 'Three-Dimensional Millimeter-Wave Imaging for Concealed Weapon Detection', Sep. 2001, IEEE Transactions on Microwave Theory and Techniques, vol. 49, No. 9, pp. 1581-1592.

Keevil, S.V., Lawinski, C.P. and Morton, E.J., 1987, "Measurement of the performance characteristics of anti-scatter grids.", Phys. Med. Biol., 32(3), 397-403.

Morton, E.J., Webb, S., Bateman, J.E., Clarke, L.J. and Shelton, C.G., 1990, "Three-dimensional x-ray micro-tomography for medical and biological applications.", Phys. Med. Biol., 35(7), 805-820.

(56) References Cited

OTHER PUBLICATIONS

Morton, E.J., Swindell, W., Lewis, D.G. and Evans, P.M., 1991, "A linear array scintillation-crystal photodiode detector for megavoltage imaging.", Med. Phys., 18(4), 681-691.
Morton, E.J., Lewis, D.G. and Swindell, W., 1988, "A method for the assessment of radiotherapy treatment precision", Brit. J. Radiol., Supplement 22, 25.
Swindell, W., Morton, E.J., Evans, P.M. and Lewis, D.G., 1991, "The design of megavoltage projection imaging systems: some theoretical aspects.", Med. Phys.,18(5), 855-866.
Morton, E.J., Evans, P.M., Ferraro, M., Young, E.F. and Swindell, W., 1991, "A video frame store facility for an external beam radiotherapy treatment simulator.", Brit. J. Radiol., 64, 747-750.
Antonuk, L.E., Yorkston, J., Kim, C.W., Huang, W., Morton, E.J., Longo, M.J. and Street, R.A., 1991, "Light response characteristics of amorphous silicon arrays for megavoltage and diagnostic imaging. ", Mat. Res. Soc. Sym. Proc., 219, 531-536.
Yorkston, J., Antonuk, L.E., Morton, E.J., Boudry, J., Huang, W., Kim, C.W., Longo, M.J. and Street, R.A., 1991, "The dynamic response of hydrogenated amorphous silicon imaging pixels.", Mat. Res. Soc. Sym. Proc., 219, 173-178.
Evans, P.M., Gildersleve, J.Q., Morton, E.J., Swindell, W., Coles, R., Ferraro, M., Rawlings, C., Xiao, Z.R. and Dyer, J., 1992, "Image comparison techniques for use with megavoltage imaging systems. ", Brit. J. Radiol., 65, 701-709.
Morton, E.J., Webb, S., Bateman, J.E., Clarke, L.J. and Shelton, C.G., 1989, "The development of 3D x-ray micro-tomography at sub 100Ã?Âµm resolution with medical, industrial and biological applications.", Presentation at IEE colloquium "Medical scanning and imaging techniques of value in non-destructive testing", London, Nov. 3, 1989.
Antonuk, L.E., Boudry, J., Huang, W., McShan, D.L., Morton, E.J., Yorkston, J, Longo, M.J. and Street, R.A., 1992, "Demonstration of megavoltage and diagnostic x-ray imaging with hydrogenated amorphous silicon arrays.", Med. Phys., 19(6), 1455-1466.
Gildersleve, J.Q., Swindell, W., Evans, P.M., Morton, E.J., Rawlings, C. and Dearnaley, D.P., 1991, "Verification of patient positioning during radiotherapy using an integrated megavoltage imaging system.", in "Tumour Response Monitoring and Treatment Planning", Proceedings of the International Symposium of the W. Vaillant Foundation on Advanced Radiation Therapy, Munich, Germany, Ed A. Breit (Berlin: Springer), 693-695.
Lewis, D.G., Evans, P.M., Morton, E.J., Swindell, W. and Xiao, X.R., 1992, "A megavoltage CT scanner for radiotherapy verification. ", Phys. Med. Biol., 37, 1985-1999.
Antonuk, L.E., Boudry, J., Kim, C.W., Longo, M.J., Morton, E.J., Yorkston, J. and Street, R.A., 1991, "Signal, noise and readout considerations in the development of amorphous silicon photodiode arrays for radiotherapy and diagnostic x-ray imaging.", SPIE vol. 1443 Medical Imaging V: Image Physics, 108-119.
Antonuk, L.E., Yorkston, J., Huang, W., Boudry, J., Morton, E.J., Longo, M.J. and Street, R.A., 1992, "Radiation response characteristics of amorphous silicon arrays for megavoltage radiotherapy imaging.", IEEE Trans. Nucl. Sci., 39,1069-1073.
Antonuk, L.E., Yorkston, J., Huang, W., Boudry, J., Morton, E.J., Longo, M.J. and Street, R.A., 1992, "Factors affecting image quality for megavoltage and diagnostic x-ray a-Si:H imaging arrays.", Mat. Res. Soc. Sym. Proc., 258, 1069-1074.
Antonuk, L.E., Boudry, J., Yorkston, J., Morton, E.J., Huang, W. and Street, R.A., 1992, "Development of thin-film, flat-panel arrays for diagnostic and radiotherapy imaging.", SPIE vol. 1651, Medical Imaging VI: Instrumentation, 94-105.
Yorkston, J., Antonuk, L.E., Seraji, N., Boudry, J., Huang, W., Morton, E.J., and Street, R.A., 1992, "Comparison of computer simulations with measurements from a-Si:H imaging arrays.", Mat. Res. Soc. Sym. Proc., 258, 1163-1168.
Morton, E.J., Antonuk, L.E., Berry, J.E., Boudry, J., Huang, W., Mody, P., Yorkston, J. and Longo, M.J., 1992, "A CAMAC based data acquisition system for flat-panel image array readout", Presentation at IEEE Nuclear Science Symposium, Orlando, Oct. 25-31, 1992.
Antonuk, L.E., Yorkston, J., Huang, W., Boudry, J., Morton, E.J. and Street, R.A., 1993, "Large area, flat-panel a-Si:H arrays for x-ray imaging.", SPIE vol. 1896, Medical Imaging 1993: Physics of Medical Imaging, 18-29.
Morton, E.J., Antonuk, L.E., Berry, J.E., Huang, W., Mody, P. and Yorkston, J., 1994, "A data acquisition system for flat-panel imaging arrays", IEEE Trans. Nucl. Sci., 41(4), 1150-1154.
Antonuk, L.E., Boudry, J., Huang, W., Lam, K.L., Morton, E.J., TenHaken, R.K., Yorkston, J. and Clinthorne, N.H., 1994, "Thin-film, flat-panel, composite imagers for projection and tomographic imaging", IEEE Trans. Med. Im., 13(3), 482-490.
Gildersleve, J., Dearnaley, D., Evans, P., Morton, E.J. and Swindell, W., 1994, "Preliminary clinical performance of a scanning detector for rapid portal imaging", Clin. Oncol., 6, 245-250.
Hess, R., De Antonis, P., Morton, E.J. and Gilboy, W.B., 1994, "Analysis of the pulse shapes obtained from single crystal CdZnTe radiation detectors", Nucl. Inst. Meth., A353, 76-79.
DeAntonis, P., Morton, E.J., T. Menezes, 1996, "Measuring the bulk resistivity of CdZnTe single crystal detectors using a contactless alternating electric field method", Nucl. Inst. Meth., A380, 157-159.
DeAntonis, P., Morton, E.J., Podd, F., 1996, "Infra-red microscopy of CdZnTe radiation detectors revealing their internal electric field structure under bias", IEEE Trans. Nucl. Sci., 43(3), 1487-1490.
Tavora, L.M.N., Morgado, R.E., Estep, R.J., Rawool-Sullivan, M., Gilboy, W.B. and Morton, E.J., 1998, "One-sided imaging of large, dense, objects using the 511 keV photons from induced pair production", IEEE Trans. Nucl. Sci., 45(3), 970-975.
Morton, E.J., 1995, "Archaeological potential of computerised tomography", Presentation at IEE Colloquium on "NDT in archaeology and art", London, May 25, 1995.
Tavora, L.M.N. and Morton, E.J., 1998, "Photon production using a low energy electron expansion of the EGS4 code system", Nucl. Inst. Meth., B143, 253-271.
Patel, D.C. and Morton, E.J., 1998, "Analysis of improved adiabatic pseudo- domino logic family", Electron. Lett., 34(19), 1829-1830.
Kundu, A and Morton, E.J., 1999, "Numerical simulation of argon-methane gas filled proportional counters", Nucl. Inst. Meth., A422, 286-290.
Luggar, R.D., Key, M.J., Morton, E.J. and Gilboy, W.B., 1999, "Energy dispersive X-ray scatter for measurement of oil/water ratios", Nucl. Inst. Meth., A422, 938-941.
Morton, E.J., Crockett, G.M., Sellin, P.J. and DeAntonis, P., 1999, "The charged particle response of CdZnTe radiation detectors", Nucl. Inst. Meth., A422, 169-172.
Morton, E.J., Clark, R.J. and Crowley, C., 1999, "Factors affecting the spectral resolution of scintillation detectors", Nucl. Inst. Meth., A422, 155-158.
Morton, E.J., Gaunt, J.C., Schoop, K., Swinhoe, M., 1996, "A new handheld nuclear material analyser for safeguards purposes", Presentation at INMM annual meeting, Naples, Florida, Jul. 1996.
Hepworth, S., McJury, M., Oldham, M., Morton, E.J. and Doran, S.J., 1999, "Dose mapping of inhomogeneities positioned in radiosensitive polymer gels", Nucl. Inst. Meth., A422, 756-760.
Morton, E.J., Luggar, R.D., Key, M.J., Kundu, A., Tavora, L.M.N. and Gilboy, W.B., 1999, "Development of a high speed X-ray tomography system for multiphase flow imaging", IEEE Trans. Nucl. Sci., 46 III(1), 380-384.
Tavora, L.M.N., Morton, E.J., Santos, F.P. and Dias, T.H.V.T., 2000, "Simulation of X-ray tubes for imaging applications", IEEE Trans. Nucl. Sci., 47, 1493-1497.
Tavora, L.M.N., Morton, E.J. and Gilboy, W.B., 2000, "Design considerations for transmission X-ray tubes operated at diagnostic energies", J. Phys. D: Applied Physics, 33(19), 2497-2507.
Morton, E.J., Hossain, M.A., DeAntonis, P. and Ede, A.M.D., 2001, "Investigation of Au-CdZnTe contacts using photovoltaic measurements", Nucl. Inst. Meth., A458, 558-562.
Ede, A.M.D., Morton, E.J. and DeAntonis, P., 2001, "Thin-film CdTe for imaging detector applications", Nucl. Inst. Meth., A458, 7-11.

(56) References Cited

OTHER PUBLICATIONS

Tavora, L.M.N., Morton, E.J. and Gilboy, W.B., 2001, "Enhancing the ratio of fluorescence to bremsstrahlung radiation in X-ray tube spectra", App. Rad. and Isotopes, 54(1), 59-72.
Menezes, T. and Morton, E.J., 2001, "A preamplifier with digital output for semiconductor detectors", Nucl. Inst. Meth. A., A459, 303-318.
Johnson, D.R., Kyriou, J., Morton, E.J., Clifton, A.G. Fitzgerald, M. and MacSweeney, J.E., 2001, "Radiation protection in interventional radiology", Clin. Rad., 56(2), 99-106.
Tavora, L.M.N., Gilboy, W.B. and Morton, E.J., 2001, "Monte Carlo studies of a novel X-ray tube anode design", Rad. Phys. and Chem., 61, 527-529.
"Morton, E.J., 1998, "Is film dead: the flat plate revolution", Keynote Talk, IPEM Annual Conference, Brighton, Sep. 14-17, 1998"\.
Luggar, R.D., Morton, E.J., Jenneson, P.M. and Key, M.J., 2001, "X-ray tomographic imaging in industrial process control", Rad. Phys. Chem., 61, 785-787.
Luggar, R.D., Morton, E.J., Key, M.J., Jenneson, P.M. and Gilboy, W.B., 1999, "An electronically gated multi-emitter X-ray source for high speed tomography", Presentation at SPIE Annual Meeting, Denver, Jul. 19-23, 1999.
Gregory, P.J., Hutchinson, D.J., Read, D.B., Jenneson, P.M., Gilboy, W.B. and Morton, E.J., 2001, "Non-invasive imaging of roots with high resolution X-ray microtomography", Plant and Soil, 255(1), 351-359.
Kundu, A., Morton, E.J., Key, M.J. and Luggar, R.D., 1999, "Monte Carlo simulations of microgap gas-filled proportional counters", Presentation at SPIE Annual Meeting, Denver, Jul. 19-23, 1999.
Hossain, M.A., Morton, E.J., and Ozsan, M.E., 2002, "Photoelectronic investigation of CdZnTe spectral detectors", IEEE Trans. Nucl. Sci, 49(4), 1960-1964.
Panman, A., Morton, E.J., Kundu, A and Sellin, P.J., 1999, "Optical Monte Carlo transport in scintillators", Presentation at SPIE Annual Meeting, Denver, Jul. 19-23, 1999.
Jenneson, P.M., Gilboy, W.B., Morton, E.J., and Gregory, P.J., 2003, "An X-ray micro-tomography system optimised for low dose study of living organisms", App. Rad. Isotopes, 58, 177-181.
Key, M.J., Morton, E.J., Luggar, R.D. and Kundu, A., 2003, "Gas microstrip detectors for X-ray tomographic flow imaging", Nucl. Inst. Meth., A496, 504-508.
Jenneson, P.M., Luggar, R.D., Morton, E.J., Gundogdu, O, and Tuzun, U, 2004, "Examining nanoparticle assemblies using high spatial resolution X-ray microtomography", J. App. Phys, 96(5), 2889-2894.
Tavora, L.M., Gilboy, W.B. and Morton, E.J., 2000, "Influence of backscattered electrons on X-ray tube output", Presentation at SPIE Annual Meeting, San Diego, Jul. 30-Aug. 3, 2000.
Wadeson, N., Morton, E.J., and Lionheart, W.B., 2010, "Scatter in an uncollimated x-ray CT machine based on a Geant4 Monte Carlo simulation", SPIE Medical Imaging 2010: Physics of Medical Imaging, Feb. 15-18, 2010, San Diego, USA.
International Search Report for PCT/GB2010/050318, dated Jul. 11, 2011.
"FISCAN Multi-power X-ray Luggage Security Check Vehicle", Wenxi Chen, et al., Technique for Police, No. 1, pp. 10-13, Dec. 31, 2000.
Morton, E.J., 2010, "Position sensitive detectors in security: Users perspective", Invited talk, STFC meeting on position sensitive detectors, RAL, May 2010.
"SureScan X1000", downloaded from https://web.archive.org/web/20030824070959/http://www.ensco.com/pdf/03.0090_SureScan_Web.pdf, downloaded Jul. 15, 2020.
"SureScan X1000", downloaded from https://web.archive.org/web/20031014195206/http://www.ensco.com:80/products/homeland/ssn/ssn_ovr.htm, downloaded Jul. 17, 2020.
H. Bruder, C. Suess, K. Stierstorfer, "Efficient extended field of view (eFOV) reconstruction techniques for multi-slice helical CT,"
Proc. SPIE 6913, Medical Imaging 2008: Physics of Medical Imaging, 69132E, (Mar. 18, 2008).
International Search Report, PCT/US2012/40923, dated Sep. 21, 2012, Rapiscan Systems, Inc.
Written Opinion of the International Searching Authority for PCT/US2010/036183, dated Aug. 20, 2010.
Written Opinion of the International Searching Authority for PCT/US2012/40923, dated Sep. 21, 2012.
*United States District Court Northern District of New York—Rapiscan Systems, Inc., Plaintiff, -vs- Surescan Corp.*, Surescan International Sales, Corp., Defendants., Civil Action No. 3:20-cv-00302-GLS-ML, Surescan's Answer to Rapiscan's First Amended Complaint for Patent Infringement, Affirmative Defenses, and Counterclaims, Jul. 6, 2020.
U.S. Appl. No. 15/235,130, filed Aug. 12, 2016.
U.S. Appl. No. 15/463,091, filed Mar. 20, 2017.
U.S. Appl. No. 15/593,943, filed May 12, 2017.
International Search Report for PCT/GB2004/001729, dated Aug. 12, 2004.
International Search Report for PCT/GB2004/001741, dated Mar. 3, 2005.
International Search Report for PCT/GB2004/001731, dated May 27, 2005.
International Search Report for PCT/GB2004/001732, dated Feb. 25, 2005.
STMicroelectronics, "Dual Full-Bridge Driver", Datasheet for L298, 2000, pp. 1-13, XP002593095.
International Search Report, PCT/US2010/41871, dated Oct. 4, 2010, Rapiscan Systems, Inc.
Bruder et al. "Efficient Extended Field of View (eFOV) Reconstructuion Techniques for Multi-Slice Helical Ct", Medical Imaging 2008: Physics of Medical Imaging, edited by Jiang Hsieh, Ehsan Samei, Proc. of SPIE vol. 6913, 69132E, (2008).
International Search Report, PCT/GB2009/001760, dated Mar. 1, 2010, Rapiscan Systems, Inc.
International Search Report for PCT/US2010/037167, dated Sep. 7, 2010.
International Search Report, PCT/US2010/37167, dated Dec. 9, 2010, Rapiscan Security Products, Inc.
Dijon et al. "Towards a low-cost high-quality carbon-nanotube field-emission display", Revised version of a paper presented at the 2004 SID International Symposium held May 25-27, 2004 in Seattle, Washington, Journal of the SID 12/4, 2004, pp. 373-378.
International Preliminary Report on Patentability for PCT/US12/40923 dated Dec. 9, 2014.
International Search Report for PCT/GB2010/050125, dated Sep. 1, 2010.
International Search Report for PCT/GB2009/051178, dated May 11, 2010.
"Efficient Extended Field of View (eFOW) Reconstruction Techniques for Multi-Slice Helical CT", H. Bruder et al, Proceedings of SPIE, vol. 6913, Mar. 6, 2008, p. 69132E, XP055179726.
Crozier et al., Performance of Turbo-Codes with Relative prime and Golden Interleaving strategies, 1999, IEEE proceedings of the Sixth International mobile satellite conference, pp. 268-275.
Sunnegard, ''Combining Analytical and Iterative Reconstruction in Helical Cone-Beam CT, 2007, Linkoping Studies in Science and Technology Thesis No. 1301.
Kohler, A Projection Access scheme for Iterative Reconstruction Based on the Golden Section, 2004, IEEE, pp. 3961-3965.
Dolinar et al., Weight Distributions for Turbo Codes Using Random and Nonrandom Permutations, 1995, TDA Progress Report 42-122, pp. 56-65.
Mouhamedou, on Distance Measurement Methods for Turbo Codes, 2005, McGill University PhD. Thesis.
Bac et al., 3D Modelling and Segmentation with Discrete Curvatures, 2005, Journal of Medical Informatics & Technologies, vol. 9, pp. 13-24.
International Search Report for PCT/US2010/036183, dated Aug. 20, 2010.
International Search Report, PCT/GB2004/001747, dated Aug. 10, 2004.

(56) References Cited

OTHER PUBLICATIONS

International Search Report, PCT/GB2004/001729, dated Aug. 12, 2004, Rapiscan Systems, Inc.
International Search Report, PCT/GB2004/001731, dated May 27, 2005.
International Search Report, PCT/GB2004/001732, dated May 27, 2005.
International Search Report, PCT/GB2004/001741, dated Mar. 3, 2005.
International Search Report for PCT/GB2006/004684, dated May 23, 2007.
International Search Report for PCT/GB2004/001747, dated Augsut 10, 2004.
International Search Report, PCT/US10/36183, dated Aug. 20, 2010.
International Search Report for PCT/GB2004/1751, dated Mar. 21, 2005.
International Search Report for PCT/GB2010/050438, dated Jun. 1, 2010.
International Search Report for PCT/US2010/036221, dated Aug. 23, 2010.
International Search Report for PCT/US2011/025777, dated Jul. 26, 2011.
Third Party Submission Under 37 CFR 1.290 for U.S. Appl. No. 15/954,853, dated Apr. 19, 2019.
International Search Report for PCT/US18/27872, dated Jul. 23, 2018.
U.S. Appl. No. 15/879,569, filed Jan. 25, 2018.
U.S. Appl. No. 12/787,930, filed May 26, 2010.
United States Provisional Patent U.S. Appl. No. 61/181,068, filed May 26, 2009.
United States Provisional Patent U.S. Appl. No. 61/155,572, filed Feb. 26, 2009.
U.S. Appl. No. 13/532,862, filed Jun. 26, 2012.
U.S. Appl. No. 13/405,117, filed Feb. 24, 2012.
U.S. Appl. No. 61/446,098, filed Feb. 24, 2011.
United States Provisional Patent U.S. Appl. No. 60/619,339, filed Oct. 15, 2004.
United States Provisional Patent U.S. Appl. No. 60/493,934, filed Aug. 8, 2003.
Definition of the term "ring" from Merriam Webster Dictionary Online, downloaded from: https://www.merriamwebster.com/dictionary/ring, downloaded Aug. 7, 2020.
Definition of the term "rotation" from Wikipedia, downloaded from: https://en.wikipedia.org/wiki/Rotation, downloaded Aug. 7, 2020.
Great Britain Patent Application No. GB0903198.0, filed Feb. 25, 2009.
Great Britain Patent Application No. GB0812864.7, filed Jul. 15, 2008.
Great Britain Patent Application No. GB0525593.0, filed Dec. 16, 2005.
Great Britain Patent Application No. GB0309379.6, filed Apr. 25, 2003.
Great Britain Patent Application No. GB0309385.3, filed Apr. 25, 2003.
Great Britain Patent Application No. GB0309374.7, filed Apr. 25, 2003.
Great Britain Patent Application No. GB0309371.3, filed Apr. 25, 2003.
Great Britain Patent Application No. GB0309383.8, filed Apr. 25, 2003.
Great Britain Patent Application No. GB0309387.9, filed Apr. 25, 2003.
United States Provisional Patent U.S. Appl. No. 61/446,098, filed Feb. 24, 2011.
*United States District Court Northern District of New York—Rapiscan Systems, Inc., Plaintiff, -vs- Surescan Corp.*, Surescan International Sales, Corp., Defendants., Civil Action No. 3:20-cv-00302-GLS-ML, Surescan'S Disclosure of Non-Infringement, Invalidity and Unenforceability Contentions, Sep. 18, 2020.
"Commericalization 1997" Success Stories, US Army Small Business Innovation Research, Army SBIR Program Management Office, U.S. Army Research Office-Washington, 5001 Eisenhower Avenu, Alexandria, Virginia 22333, 1997.
William Michael Thompson's Thesis entitled "Source Firing Patterns and Reconstruction Algorithms for a Switched Source, Offset Detector CT Machine," dated Dec. 31, 2010, and submitted to the University of Manchester ("Thompson Thesis").
U.S. Appl. No. 12/097,422, filed Jun. 13, 2008.

\* cited by examiner

| Parameter | Vary tube current | | | Vary source rotation speed | | | | Vary conveyor speed | | | | Vary number of detector rings | | | |
|---|---|---|---|---|---|---|---|---|---|---|---|---|---|---|---|
| Tube Voltage (kV) | 160 | 160 | 160 | 160 | 160 | 160 | 160 | 160 | 160 | 160 | 160 | 160 | 160 | 160 |
| Tube Current (mA) | 20 | 10 | 5 | 20 | 20 | 20 | 20 | 20 | 20 | 20 | 20 | 20 | 20 | 20 |
| Reconstructed image SNR | 120 | 85 | 60 | 120 | 170 | 240 | 120 | 120 | 450 | 120 | 170 | 240 |
| | | | | | | | | | | | | | | | |
| Conveyor Speed (m/s) | 0.5 | 0.5 | 0.5 | 0.5 | 0.5 | 0.5 | 0.5 | 0.25 | 0.125 | 0.5 | 0.5 | 0.5 |
| Bag Throughput (bags/hr) | 1800 | 1800 | 1800 | 1800 | 1800 | 1800 | 1800 | 900 | 450 | 1800 | 1800 | 1800 |
| | | | | | | | | | | | | | | | |
| Source revolutions per second | 30 | 30 | 30 | 30 | 15 | 7.5 | 30 | 30 | 30 | 30 | 30 | 30 |
| Number of detector rings | 8 | 8 | 8 | 8 | 8 | 8 | 8 | 8 | 8 | 8 | 4 | 2 |
| Number of reconstructed slices per second | 480 | 480 | 480 | 480 | 240 | 120 | 480 | 480 | 480 | 480 | 240 | 120 |
| Reconstructed pixel size, Z-axis (mm) | 1.04 | 1.04 | 1.04 | 1.04 | 2.08 | 4.17 | 1.04 | 0.52 | 0.26 | 1.04 | 2.08 | 4.17 |

*FIG. 3*

*Performance Characteristics*

| Parameter | Standard operating characteristics | | | |
|---|---|---|---|---|
| Tube Voltage (kV) | 160 | 160 | 160 | 160 |
| Tube Current (mA) | 20 | 20 | 20 | 20 |
| Reconstructed image SNR | 85 | 120 | 170 | 240 |
| Conveyor Speed (m/s) | 1.0 | 0.5 | 0.25 | 0.125 |
| Bag Throughput (bags/hr) | 3600 | 1800 | 900 | 450 |
| Source revolutions per second | 60 | 30 | 15 | 7.5 |
| Number of detector rings | 8 | 8 | 8 | 8 |
| Number of reconstructed slices per second | 960 | 480 | 240 | 120 |
| Reconstructed pixel size, Z-axis (mm) | 1.04 | 1.04 | 1.04 | 1.04 |

*FIG. 4*

*Standard Operating Characteristics*

| Energy | 30kVp | 40kVp | 50kVp | 60kVp | 70kVp | 80kVp | 90kVp | 100kVp | 110kVp | 120kVp | 130kVp | 140kVp | 150kVp |
|---|---|---|---|---|---|---|---|---|---|---|---|---|---|
| Summary of individual detector response | | | | | | | | | | | | | |
| MeV in crystal | 2.30E-03 | 4.54E-01 | 5.55E+00 | 2.40E+01 | 6.39E+01 | 1.37E+02 | 2.40E+02 | 3.70E+02 | 5.23E+02 | 6.96E+02 | 8.86E+02 | 1.09E+03 | 1.31E+03 |
| Optical Photons | 7.36E+01 | 1.45E+04 | 1.77E+05 | 7.70E+05 | 2.05E+06 | 4.37E+06 | 7.69E+06 | 1.18E+07 | 1.67E+07 | 2.23E+07 | 2.84E+07 | 3.49E+07 | 4.19E+07 |
| Signal current (nA) | 0.00 | 0.02 | 0.24 | 1.04 | 2.78 | 5.94 | 10.43 | 16.07 | 22.71 | 30.22 | 38.50 | 47.43 | 56.91 |
| Integrated charge (pC) | 0.00 | 0.00 | 0.02 | 0.09 | 0.24 | 0.52 | 0.91 | 1.39 | 1.97 | 2.62 | 3.34 | 4.12 | 4.94 |
| Number of 80keV photons | 0 | 6 | 69 | 301 | 799 | 1708 | 3002 | 4624 | 6533 | 8695 | 11077 | 13646 | 16373 |
| Summary of reconstructed image quality | | | | | | | | | | | | | |
| SNR in reconstructed pixel | 0 | 2 | 7 | 14 | 23 | 34 | 45 | 56 | 66 | 76 | 86 | 96 | 105 |

FIG. 12

X-RAY SCANNING SYSTEM WITH STATIONARY X-RAY SOURCES

CROSS-REFERENCE

The present application is a continuation of U.S. patent application Ser. No. 12/712,476, filed on Feb. 25, 2010, entitled "X-Ray Scanners" (the "'476 Application")

The '476 Application relies on U.S. Patent Provisional Application No. 61/155,572 filed on Feb. 26, 2009. The '476 Application also relies on Great Britain Patent No. GB0903198.0, filed on Feb. 25, 2009, for foreign priority.

The '476 Application is also a continuation-in-part of U.S. patent application Ser. No. 12/485,897, filed on Jun. 16, 2009, which is a continuation of U.S. patent application Ser. No. 10/554,656, filed on Oct. 25, 2005, which is a 371 national stage application of PCT/GB04/01729, which was filed on and relies on for priority UK Patent Application No. 0309387, filed on Apr. 25, 2003.

The '476 Application is also a continuation-in-part of U.S. patent application Ser. No. 12/371,853, filed on Feb. 16, 2009, which is a continuation of U.S. patent application Ser. No. 10/554,975, filed on Oct. 25, 2005, which is a national stage application of PCT/GB2004/01741, filed on Apr. 23, 2004 and which, in turn, relies on Great Britain Application Number 0309383.8, filed on Apr. 25, 2003, for priority.

The '476 Application is also a continuation-in-part of U.S. patent application Ser. No. 12/651,479, which is a continuation of U.S. patent application Ser. No. 10/554,654, filed on Oct. 25, 2005, which is a national stage application of PCT/GB2004/001731, filed on Apr. 23, 2004, which relies on Great Britain Patent Application Number 0309371.3, filed on Apr. 25, 2003 for priority.

The '476 Application is also a continuation-in-part of U.S. patent application Ser. No. 12/364,067, which is a continuation of U.S. patent application Ser. No. 12/033,035, which is a continuation of U.S. patent application Ser. No. 10/554,569, filed on Oct. 25, 2005, which is a national stage filing of PCT/GB04/001732, having a priority date of Apr. 25, 2003.

The '476 Application is also a continuation-in-part of U.S. patent application Ser. No. 12/211,219, filed on Sep. 16, 2008, which is a continuation of U.S. patent Ser. No. 10/554,655, which is a national stage application of PCT/GB2004/001751, filed on Apr. 23, 2004, having a priority date of Apr. 25, 2003.

The '476 Application is also a continuation-in-part of U.S. patent application Ser. No. 10/554,570, which is a national stage application of PCT/GB2004/001747, filed on Apr. 23, 2004, having a priority date of Apr. 25, 2003.

The '476 Application is also a continuation-in-part of U.S. patent application Ser. No. 12/097,422, filed on Jun. 13, 2008, which is a national stage application of PCT/GB2006/004684, filed on Dec. 15, 2006 and relies on Great Britain Patent Application Number 0525593.0, filed on Dec. 16, 2005, for priority.

Each of the aforementioned PCT, foreign, and U.S. applications is herein incorporated by reference in their entirety.

FIELD OF THE INVENTION

The present invention relates to X-rays scanners and scanner systems. It has particular application in scanner systems for scanning baggage and cargo, but can also be used in other types of X-ray scanner.

BACKGROUND OF THE INVENTION

In typical computed tomography systems, X-rays, generated by an X-ray source, are collimated to form a fan beam that is transmitted through an imaged object to an X-ray detector array orientated within the imaging plane. The detector array is comprised of detector elements which each measure the intensity of transmitted radiation along a ray projected from the X-ray source to that particular detector element. The X-ray source and detector array are typically rotated on a gantry within the imaging plane, around the imaged object, so that the fan beam intercepts the imaged object at different angles. At each angle, a projection is acquired comprised of the intensity signals from each of detector elements. The gantry is then rotated to a new angle and the process is repeated to collect a number of projections at different angles to form a tomographic projection set. In alternate tomography systems, the detector array remains fixed and comprises a 360 degree ring of detectors and the source is moved arcwise around the imaged object through 180 degrees plus the fan beam angle or more of arc. In such systems, only the X-ray source is rotated to acquire the tomographic projection set.

The time and expense of a tomographic study increases with the number of slices required. The time required to collect the data for a series of slices depends in part on aspects such as a) the time required to accelerate the gantry to scanning speed, b) the time required to obtain a complete tomographic projection set, c) the time required to decelerate the gantry and d) the time required to reposition the object in the z-axis for the next slice. Reducing the time required to obtain a full slice series may be accomplished by reducing the time required to complete any of these four steps. Additionally, movement of the object under inspection as well as the motion of the X-ray source and/or detector array, using the gantry, results in creation of unacceptably high levels of artefact in reconstructed images.

Accordingly, there is need in the prior art to reduce the overall time of conducting a tomographic inspection. There is also need to improve the overall imaging quality of tomographic inspection by addressing causes leading to image artefacts—particularly those induced by physical motion of the source-detector assembly.

SUMMARY OF THE INVENTION

It is an object of the present invention to provide an X-ray scanner comprising an X-ray source arranged to emit X-rays from a plurality of source points through an imaging volume. The scanner may further comprise an array of X-ray detectors which may be arranged around the imaging volume and may be arranged to output detector signals in response to the detection of X-rays. The scanner may further comprise a conveyor arranged to convey an object through the imaging volume in a scan direction, and may also comprise at least one processor arranged to process the detector signals to produce an image data set defining an image of the object. The image may be a two dimensional image or a three dimensional image. The image may have a resolution in the scan direction that is at least 90% as high as in one direction, and in some cases two directions, orthogonal to the scan direction. For a three dimensional image the resolution in the scan direction may be at least 90% as high, or may be as high in the scan direction as the average of the resolutions in two other orthogonal directions. In some embodiments the resolution in the scan direction may be higher, for example at least 20% or in some cases 50% higher, than the resolution in one, or two, other orthogonal directions. The image may have a resolution in at least two directions, the scan direction (R1) and a direction orthogonal to the scan direction (R2). In some embodiments of the present invention, R1≥(0.90)*R2. In some cases R1≥R2.

The resolution in the scan direction may be substantially equal to the resolution in the other two directions. For example the resolutions may all be within 10% of each other, and preferably within 5% of each other.

The source points may be arranged in a plane perpendicular to the scan direction. The detectors of the array may be located in a plane which is perpendicular to the scan direction, or a plurality of such planes.

The detector array may be offset from the source points in the scan direction. The detector array may be at least two detectors wide in the scan direction, and may for example be up to six or eight detectors wide, or in some cases up to ten detectors wide in the scan direction. The detectors may be arranged in a plurality of rings, the rings being in respective planes, which may be spaced from each other in the scan direction. In this case there may be ten rings or less, or in some cases eight rings or less, or even six rings or less. The detectors may have a width in a circumferential direction and each detector may be offset in the circumferential direction from one adjacent to it in the scan direction. Each detector may have a width in the circumferential direction and the offset is less than the width.

The scanner may further comprise a controller arranged to activate each of the source points in a predetermined sequence, once in each of a sequence of scan cycles. The controller may be arranged to control the frequency of the scan cycles so that it takes an integer number, which may be greater than one, of scan periods for the object to move a distance in the scan direction equal to the spacing of the detectors in the scan direction.

The scan cycle frequency may be variable so that the resolution in the scan direction can be adjusted. The control means may be arranged to adjust the scan frequency so as to provide a constant resolution in the scan direction for a plurality of object speeds.

The conveyor may be arranged to convey the object at a speed of at least 0.1 m/s, or at least 0.5 m/s, or at least 1.0 m/s. The scanner may be arranged to generate an image data set having a signal to noise ratio of at least 60, or at least 80, or at least 100. The image may be made up of voxels having a size in the scan direction of 5 mm or less, or 4 mm or less, or 3 mm or less, or 2 mm or less, or 1.1 mm or less. The image voxels may have a size in the two directions orthogonal to the scan direction which is 5 mm or less, or 4 mm or less, or 3 mm or less, or 2 mm or less, or 1.1 mm or less.

Some embodiments of the invention can provide a motionless X-ray imaging system able to generate reconstructed three-dimensional X-ray images with a conveyor speed of 0.25 m/s to 1.0 m/s, corresponding to a throughput of 800 to 3000 items per hour, for scanned objects of length 1 m in the scan direction and spaced along the conveyor with a slot length of 1.2 m in the scan direction, with equal spatial resolution in all dimensions (2 mm and better) with a reconstructed pixel size of 1.5 mm×1.5 mm×1.5 mm or less with a reconstructed image signal-to-noise ratio of 50 or better, and typically in excess of 100, with no more than eight rings of X-ray detectors.

The present invention further provides a mobile scanning system comprising a vehicle comprising a body and a scanner housed within the body wherein the scanner comprises X-ray source means arranged to generate X-rays from a plurality of source points, an array of X-ray detectors arranged to detect X-rays from the source points, and control means arranged to activate each of the source points so as to scan an imaging volume. The system may include a single conveyor extending through the system. It may be split into two conveyor sections, one for in-feed and one for out-feed, but preferably has a single belt that passes across both sections.

The present invention further provides a modular scanner system comprising a scanner section, an input conveyor section comprising a conveyor arranged to convey items towards the scanner section and an output conveyor section comprising a conveyor arranged to move items away from the scanner section, wherein at least one of the conveyor sections is detachably connected to the scanner section.

The present invention further provides an X-ray scanner system comprising an X-ray source arranged to emit X-rays from a plurality of source points through an imaging volume, an array of X-ray detectors arranged to output detector signals in response to the detection of the X-rays, a controller arranged to activate each of the source points in turn, at least one processor arranged to process the detector signals to produce an image data set corresponding to each of a plurality of views of an object, and a user interface arranged to receive a plurality of different user inputs and a display arranged to display each of the views in response to a respective one of the inputs. The user interface may comprise one or more input members, such as input buttons, which can be pressed or otherwise operated to provide the inputs. For example the user interface may include a mouse. Alternatively it may comprise a touch screen with different areas which can be touched to provide the different inputs.

The present invention further provides a scanner system comprising an X-ray source and an array of X-ray detectors defining a scanning volume, an input conveyor arranged to convey items into the scanning volume and an exit conveyor arranged to convey items away from the scanning volume, first and second input sensors arranged to detect the presence of an item at first and second positions on the input conveyor and first and second exit sensors arranged to detect the presence of an item at first and second positions on the exit conveyor, and control means arranged to control activation of the X-ray source in response to signals from the sensors.

BRIEF DESCRIPTION OF THE DRAWINGS

These and other features and advantages of the present invention will be appreciated, as they become better understood by reference to the following detailed description when considered in connection with the accompanying drawings:

FIG. 3 is a table of exemplary, but not limiting, performance characteristics of the system of FIG. 1;

FIG. 4 is a table of exemplary, but not limiting, operating characteristics for one mode of operation of the system of FIG. 1;

FIG. 12 is a table of exemplary, but not limiting, operating characteristics for one mode of operation of the system of FIG. 1;

DETAILED DESCRIPTION

Various modifications to the preferred embodiment, disclosed herein, will be readily apparent to those of ordinary skill in the art and the disclosure set forth herein may be applicable to other embodiments and applications without departing from the spirit and scope of the present invention and the claims hereto appended. Thus, the present invention is not intended to be limited to the embodiments described, but is to be accorded the broadest scope consistent with the disclosure set forth herein.

Figure 1:
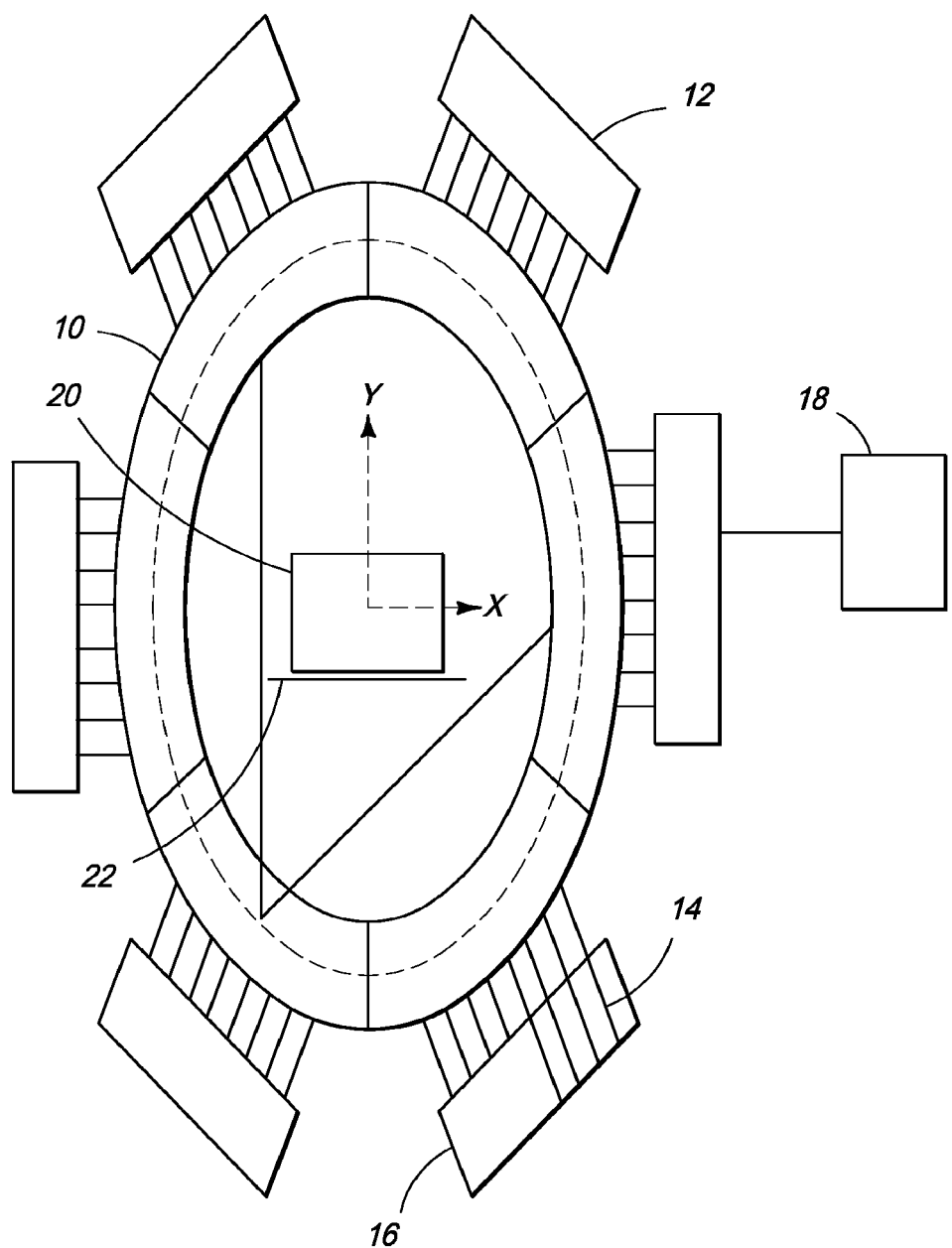
FIG. 1 is a transverse section through a scanner system according to an embodiment of the invention.

Referring to FIG. 1, in one embodiment of the present invention, an X-ray scanner comprises one or more X-ray tubes 10 which are configured into a substantially circular arrangement around the scanner axis wherein each X-ray tube 10 contains an X-ray source having one or more X-ray source points 12. The emission of X-rays from each source point 12 in each of the X-ray tubes 10 is controlled by a switching circuit 14, with one independent switching circuit for each X-ray source point. The switching circuits for each tube 10 together form part of a control circuit 16 for that tube. A controller 18 controls operation of all of the individual switching circuits 14. The switching circuits 14 are controlled to fire in a pre-determined sequence such that in each of a series of activation periods, fan-shaped beams of X-rays from one or more active source points propagate through an object 20 which is mounted on a conveyor 22 towards the centre of the arrangement of X-ray tubes 10.

Figure 2:
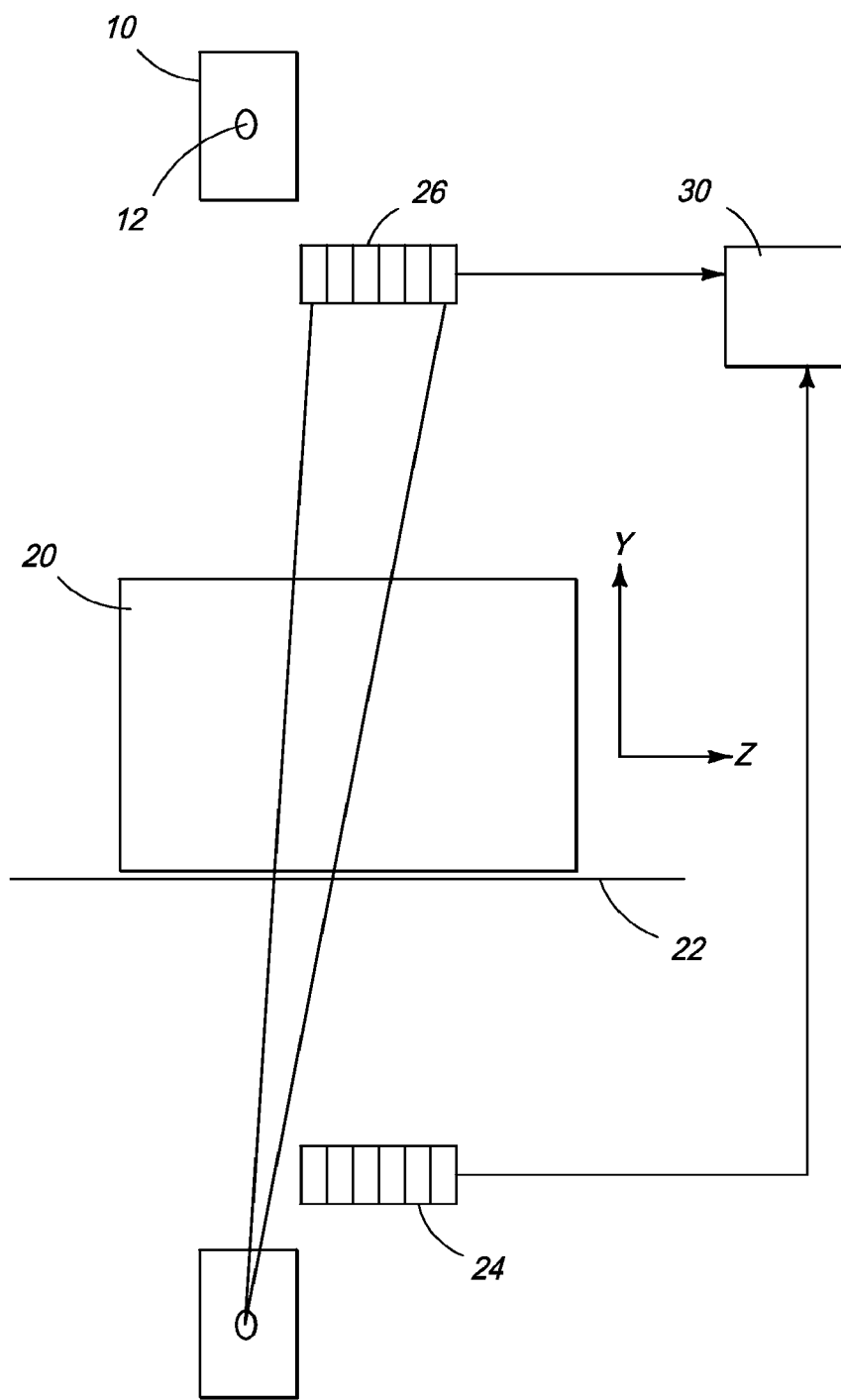
FIG. 2 is a longitudinal section through the scanner system of FIG. 1.

Referring to FIG. 2, the scanner further comprises an array of X-ray detectors 24 extending around the scanner axis. The detector array is made up of a number of detector rings 26. Each ring is in a plane perpendicular to the scanner axis or a plurality of such planes. The scanner axis is referred to as the Z-direction and the two orthogonal directions, one horizontal and one vertical, are referred to as the X-direction and the Y-direction. The source points 12, in one embodiment, are arranged in a plane perpendicular to the scan direction.

The X-Y plane or planes in which the X-ray tube source points 12 are located are offset from the planes of the X-ray detectors 24 such that there is an unobstructed path, except for the conveyor 22 and the object 20 under inspection, from each active source point 12 to its associated set of X-ray detectors 24. Thus, in one embodiment, the detectors 24 have a width in a circumferential direction and each detector is offset in the circumferential direction from one adjacent to it in the scan direction. Each detector has a width in the circumferential direction and the offset is less than the width, in one embodiment.

In one embodiment, the detector array 24 is at least two detectors wide in the scan direction, and may for example be up to six or eight detectors wide, or in some cases up to ten detectors wide in the scan direction. As mentioned earlier, the detectors may be arranged in a plurality of rings, the rings being in respective planes, which may be spaced from each other in the scan direction. In this case there may be ten rings or less, or in some cases eight rings or less, or even six rings or less. In alternate embodiments, the detectors may be arranged in one or more helical arrays.

A processor 30 is arranged to receive the signals output by all of the detectors 24 and forms an X-ray re-construction engine arranged to process the detector signals. As the X-ray source points 12 are switched according to a pre-determined sequence, the detector signals are digitized and transmitted to the X-ray reconstruction engine 30 which produces a reconstruction of the object 20 that is present in the beam. It is advantageous to select a sequence of X-ray source point activation which maximises the quality of the reconstructed image. The reconstruction engine 30 produces from the detector signals one image data set for each activation of each source point 12. Each source point is activate once in each of a series of scan cycles. The data sets for one cycle can be combined to generate a three dimensional image of a slice of the item, and a series of such image data sets built up as the item moves through the scanner in the Z-direction can be built up into a full three dimensional image data set of the item. Also the data sets from one source point collected as the item moves through the scanner can be built up to form a two-dimensional image data set of the item.

An exemplary sequence provides X-ray emission from sources points that rotate around the conveyor and object under inspection in a plane substantially perpendicular to the direction of motion of the conveyor and object under inspection. For example there may be four source points, which may be equally spaced around the Z axis. Of course, other scanning sequences may be adopted as required to optimise the image reconstruction method.

It is generally reasonable to consider an optimization of the X-ray imaging system to the activity for which the system is to be deployed. With specific reference to X-ray screening of baggage and cargo items, it is highly advantageous to achieve equal resolution in all three dimensions. This substantially assists in the detection of materials that may be conformed into sheet-like structures. Further, it is highly advantageous to achieve this equally matched resolution at high conveyor speeds, for example in the range 0.25 m/s to 1 m/s.

In the embodiment described with reference to FIGS. 1 and 2, a motionless X-ray imaging system is able to generate reconstructed three-dimensional X-ray images with a conveyor speed of 0.25 m/s to 1.0 m/s, corresponding to a throughput of 800 to 3000 items per hour with equal spatial resolution in all dimensions (2 mm and better) with a reconstructed pixel size of 1.5 mm×1.5 mm×1.5 mm or less with a reconstructed image signal-to-noise ratio of 50 or better, and typically in excess of 100, with no more than eight rings of X-ray detectors.

Advantageously, an X-ray system of this type may be further optimized to deliver a spatial resolution in the scan direction (parallel to the conveyor) whose spatial resolution exceeds that of the in-plane spatial resolution (perpendicular to the plane of the conveyor). In one embodiment, the X-ray scanner of the present invention is optimized to deliver image resolution in the scan direction that is at least 90% as high as in one direction, and in some cases two directions, orthogonal to the scan direction. In another embodiment, for a three dimensional image the resolution in the scan direction may be at least 90% as high, or may be as high in the scan direction as the average of the resolutions in two other orthogonal directions. In alternate embodiments the resolution in the scan direction may be higher, for example at least 20% or in some cases 50% higher, than the resolution in one, or two, other orthogonal directions. Again, the resolution in the scan direction may be substantially equal to the resolution in the other two directions. For example the resolutions may all be within 10% of each other, and preferably within 5% of each other in further embodiments.

X-ray image may have a resolution in at least two directions, the scan direction ($R_1$) and a direction orthogonal to the scan direction ($R_2$). In some embodiments of the present invention, $R_1 \geq (0.90)*R_2$. In some cases $R_1 \geq R_2$.

FIG. 3 provides exemplary, but not limiting, performance characteristics for an X-ray scanner of the type shown in FIGS. 1 and 2. These figures are provided as an example of the performance of a system that has been optimized for the purpose of screening baggage and cargo items. In other embodiments the tube voltage may be in the range from 100 kV to 200 kV, and preferably in the range from 150 kV and 180 kV. The tube current can be in the range from 2 and 30 mA, but preferably in the range from 4 to 25 mA, or in the range from 5 to 20 mA as in the examples shown. The number of reconstruction slices per second may be at least 100, and may be in the range from 100 to 1000, and preferably at least 200. In some cases at least 300 or at least 400 may be needed.

It shall be understood by one skilled in the art that the reconstructed image signal-to-noise figures are affected by the design of the X-ray sensor (for example by the sensor area, by the sensor detection efficiency, by the noise of the associated readout electronics and by timing jitter in the switching of the X-ray source points and the data acquisition system), and that the information presented in this regard in FIG. 3 is for one particular detector configuration only.

Generally, it is understood that the in-plane reconstructed pixel size shall be determined based on overall acceptable data rate at the output of the image reconstruction process and on the spatial resolution of the imaging data based on the optimised sensor configuration. A suitable reconstructed pixel size to match the system performance characteristics as shown in FIG. 3 is in the range 1 mm to 2 mm and typically 1.2 mm×1.2 mm.

It is further possible to establish suitable operating characteristics for operation of an X-ray imaging system with varying conveyor speed. As described in FIG. 4, a set of exemplary, but not limiting, operating characteristics for a particular system optimisation show operation of the system with conveyor speeds from 1 m/s to 0.125 m/s. Here, the optimization seeks to maintain an identical spatial resolution and an associated reconstructed pixel dimension 1.04 mm in the scan direction independent of conveyor speed without changing the sensor configuration. This is achieved by adjusting the scan frequency, i.e. the frequency of the scan cycles, in proportion to the speed of the conveyor. In one embodiment the conveyor speed is at least 0.1 m/s, or at least 0.5 m/s, or at least 1.0 m/s.

In some embodiments the tube current can be controlled so that it varies in direct proportion to the conveyor speed. This can provide a constant signal-to-noise ratio which is independent of scan speed. For example if the scan speed is doubled then the tube current would be doubled, and if the scan speed is halved the tube current is also halved.

Such a practical optimization allows the performance of the X-ray system to be altered dynamically based on imaging load. At times when high throughput is required, the conveyor speed may be set to a fast speed with a reduction in reconstructed image signal to noise ratio. At times of low throughput, the conveyor speed may be reduced to a lower speed with an associated improvement in reconstructed image signal-to-noise ratio.

According to an aspect of the present invention, the image quality for the X-ray scanner of the present invention as shown in FIGS. 1 and 2, is optimized with respect to a set of parameters. For image quality estimation and optimization, X-ray spectrum emitted by the X-ray source is propagated to an X-ray detector of suitable size, location and composition for detection of primary X-ray beam from the source.

In one embodiment, the X-ray detector used is a scintillation detector with photodiode electronics readout system.

Signal-to-Noise Ratio (SNR)

For the X-ray scanner of the present invention, FIG. 12 is a table showing exemplary, but not limiting, operating characteristics for the X-ray source operating at 20 mA with an 800 mm diameter reconstruction circle, an 8-ring X-ray detector array and a reconstructed scan rate of 240 slices per second. It is observed from the data of FIG. 12 that the reconstructed image signal-to-noise ratio (SNR) is strongly dependent on tube voltage. The higher the tube voltage, the better the reconstructed image signal-to-noise ratio (SNR).

Figure 13:
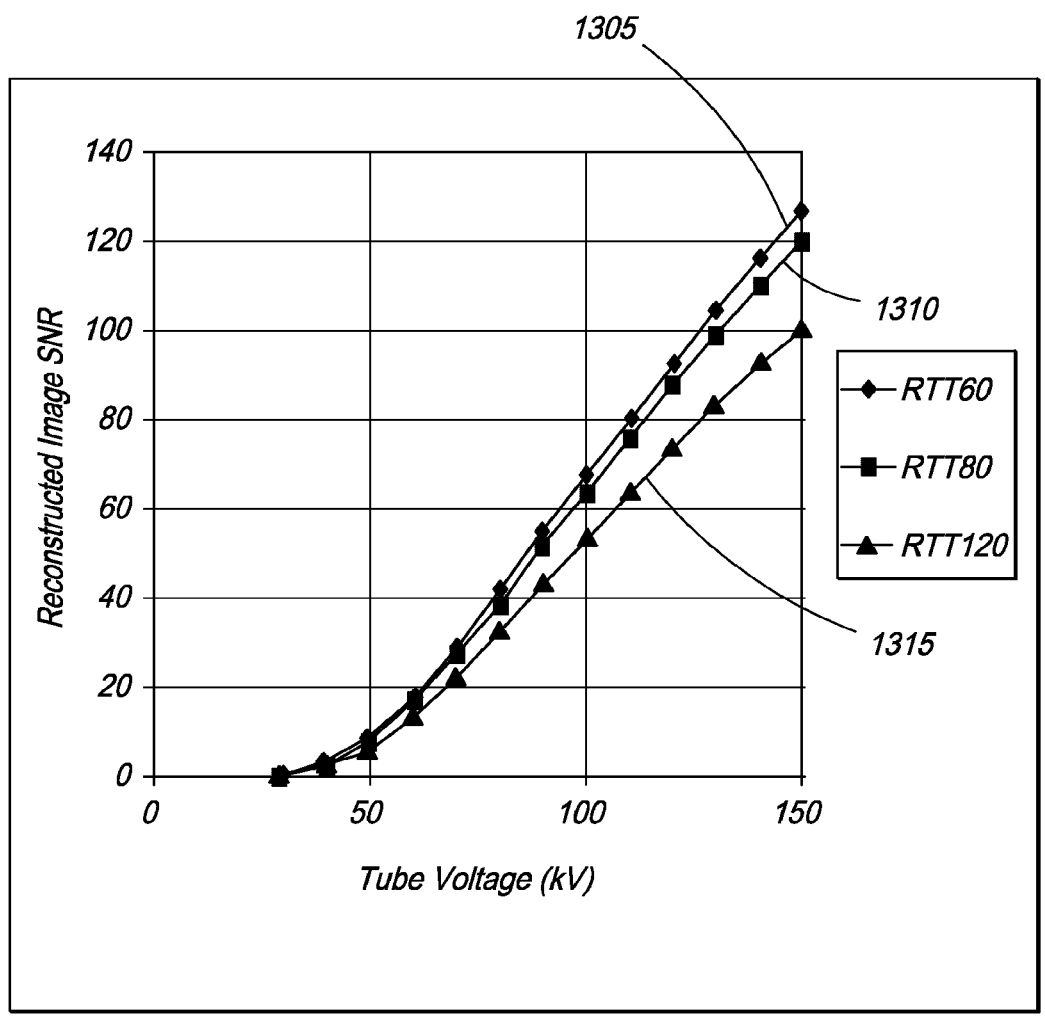
FIG. 13 is a graph showing variation of reconstructed signal-to-noise ratio with respect to tube voltage for the system of FIG. 1.

FIG. 13 shows variation of reconstructed signal-to-noise ratio with respect to tube voltage for the X-ray scanner of the present invention when operated with a beam current of 20 mA and a reconstruction rate of 240 frames per second with 8 detector rings for reconstructed image diameters of 60 cm (1305), 80 cm (1310) and 120 cm (1315) each with 1 mm×1 mm×1 mm reconstructed voxel dimension. Persons of ordinary skill in the art would appreciate that a 1 mm×1 mm×1 mm voxel size suits security inspection applications while a signal-to-noise ratio of over 100 provides the level of quantitative image that is required in many practical applications.

Accordingly the X-ray scanner of FIGS. 1 and 2 of the present invention is optimized for signal-to-noise by aiming for a balance in cost, complexity and performance. In one embodiment, the scanner is optimized to generate an image data set having a signal to noise ratio of at least 60, or at least 80, or at least 100. The image is made up of voxels having a size in the scan direction of 5 mm or less, or 4 mm or less, or 3 mm or less, or 2 mm or less, or 1.1 mm or less. The image voxels have a size in the two directions orthogonal to the scan direction which is 5 mm or less, or 4 mm or less, or 3 mm or less, or 2 mm or less, or 1.1 mm or less.

In one embodiment the X-ray scanner of the present invention provides a motionless X-ray imaging system able to generate reconstructed three-dimensional X-ray images with a conveyor speed of 0.25 m/s to 1.0 m/s, corresponding to a throughput of 800 to 3000 items per hour with equal spatial resolution in all dimensions (2 mm and better) with a reconstructed pixel size of 1.5 mm×1.5 mm×1.5 mm or less with a reconstructed image signal-to-noise ratio of 50 or better, and typically in excess of 100, with no more than eight rings of X-ray detectors.

Contrast

Contrast in the X-ray scanner of the present invention is defined as 1/SNR, where SNR is signal-to-noise ratio. Referring FIG. 12, in one embodiment, at 150 kVp the contrast that may be resolved in an open field image is determined as (1/105)×100%=0.95%. The smaller this number is the better the contrast resolution of the imaging system. Persons of ordinary skill in the art should note that contrast in a region containing an object which attenuates an X-ray beam will be less than in an open field region since the number of X-ray photons that penetrate through that region will be less than in an open field region.

Dynamic Range

Dynamic range is defined as (full-scale signal)/(dark noise). The dark noise is obtained by switching off the X-ray source while leaving the detectors and image reconstruction system active. If this dark level is normalized to zero and the light level (i.e. that intensity which is reconstructed with the X-ray beam switched on with no object in the beam) is normalized to 1000, the dynamic range is equal to 1000/(standard deviation in the dark image). An optimized X-ray scanner of the present invention, in one embodiment, provides a reconstructed dark noise of the order of 0.1% of full scale or less, thereby resulting in a dynamic range of 1000 or more.

The overall X-ray scanner dynamic range is dependent on the noise of the electronics readout system used. Thus, the noisier the electronics readout system, the worse the overall scanner dynamic range. Electronics readout system noise depends at least on the design of the photodiode, on the layout and length of the signal traces that lead from the photodiode sensors, on the design of the input electronics stage and on the resolution of the analogue-to-digital converter that follows its front end amplifier.

Figure 14:
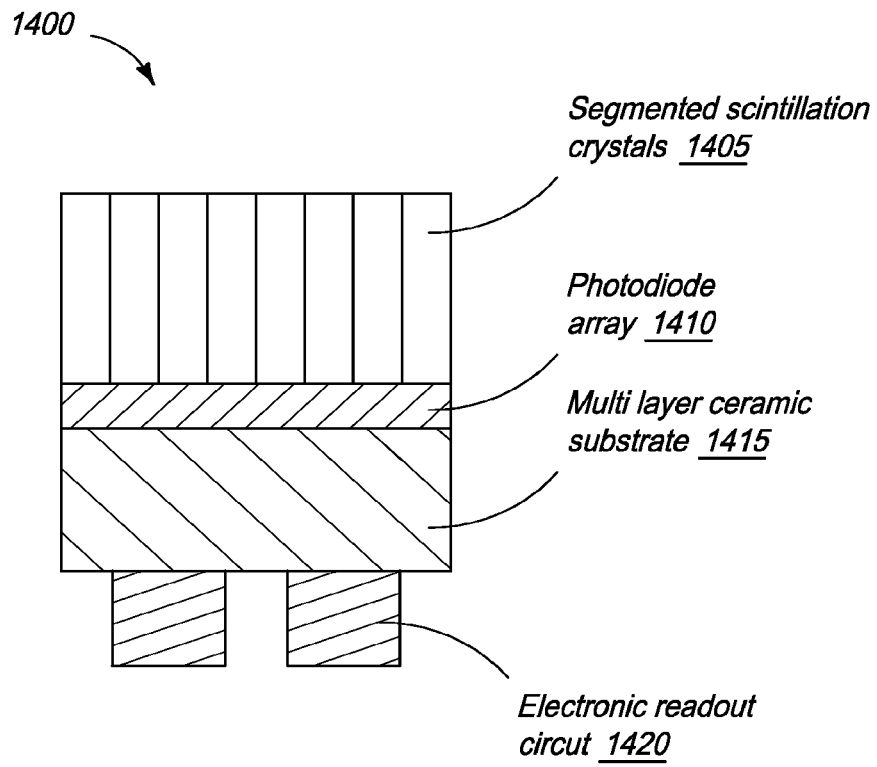
FIG. 14 shows an embodiment of scintillation detector with photodiode electronics readout used in operation of the system of FIG. 1.

To achieve a wide dynamic range, the X-ray scanner of the present invention uses a scintillation detector 1400 with photodiode electronics readout as shown in FIG. 14. In one embodiment, the individual segmented scintillation crystals 1405 of the scintillation detector 1400 are glued together with tungsten foil septa. The tungsten septa prevent optical cross-talk between individual crystals. The septa stop energetic Compton recoil and photoelectrons transferring signal between adjacent scintillation crystals to reduce cross-talk between adjacent crystals.

A reverse illuminated photodiode array 1410 with thin common cathode entrance window is adhered, glued, or otherwise attached to the base of the scintillation crystal array 1405. Optical photons from the scintillator 1405 pass through a thin optical coupling, further through a thin passivation/contact layer in the photodiode and into the bulk region of the photodiode. Charge generated in the depletion region drift under the influence of an applied bias towards a set of anodes—one anode contact region per scintillation crystal. The anode is advantageously constructed so as to minimize cross-talk of drift electrons from one pixel to another. The photodiode array 1410 is then bump bonded to a patterned substrate 1415 using, for example, a conductive epoxy pad on an indium bump bond with backfill of adhesive to ensure good adherence of the photodiode/crystal array to the substrate 1415.

The multi-layer ceramic substrate 1415 is advantageously drilled, printed with conductive ink and fired at high temperature to produce a multi-layer circuit card with pads on one side that match the layout of anodes on the photodiode array 1410 and on the other side match the pads on suitable electronic readout circuits 1420. The thermal expansion coefficient of the ceramic substrate 1415 and photodiode 1410 are matched to provide good thermal stability during firing of the adhesives and during bump bonding.

The electronic readout circuit 1420 is advantageously either soldered or fixed to the ceramic substrate 1415 using conductive epoxy pads. A low density connector then takes electrical signals from the front-end electronics to subsequent signal processing circuitry. In this way, the scintillator detector 1400 has minimum trace lengths and hence low intrinsic capacitance which helps to maximise dynamic range of the X-ray scanner of the present invention.

Linearity

Intrinsic linearity of an X-ray system depends on aspects such as filtering of the X-ray spectrum emitted from X-ray source, X-ray tube operating voltage, filtering of the X-ray beam prior to X-ray detectors and the material from which the X-ray detector is fabricated. Also, degradation of X-ray system linearity is caused by detection of X-rays which have scattered from the object under investigation and on X-rays which scatter from the components of the X-ray system itself.

Figure 15:
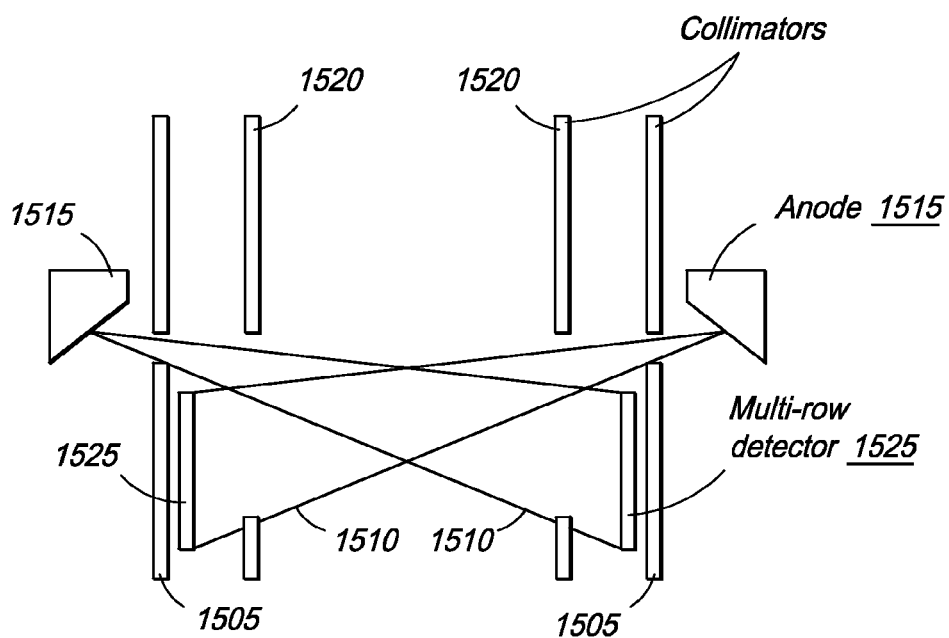
FIG. 15 shows an embodiment of collimation and radiation shielding structures to reduce scatter during operation of the system of FIG. 1.

Therefore, the X-ray scanner of the present invention uses collimation and radiation shielding structures to reduce scatter. FIG. 15 shows an embodiment of the shielding system used in the X-ray scanner of FIGS. 1 and 2 of the present invention. FIG. 15 shows how the first set of collimators 1505 shield the primary beam 1510 as it is emitted from X-ray tube 1515 and how the second set of collimators 1520 again provide shielding before the beam 1510 reaches X-ray detectors 1525. In one embodiment of the optimized X-ray scanner of the present invention, a scatter fraction of the order of 1% is achieved in open field conditions.

The X-ray scanner optimized for low scatter also results in maximizing its contrast performance. The signal-to-noise ratio (SNR) of an X-ray system, the noise performance of which is dominated by X-ray photon noise, is defined as:

$$SNR = \frac{\text{Mean}}{S.D.} = \frac{\sigma^2}{\sigma} = \sigma$$

In other words, the signal-to-noise ratio (SNR) is simply the standard deviation of the photon signal. However, in the presence of X-ray scatter, the situation is changed such that the standard deviation, $\sigma^2$, comprises noise due both to the primary signal as well as due to scatter:

$$SNR = \frac{\sigma^2}{\sigma + \sigma_s}$$

A scatter fraction of 1% of primary beam intensity results in a reduction of SNR by a similar amount. The distribution of scattered radiation at the detectors is approximately constant independent of position in the array for a given object density. Thus, the impact of scatter is more significant in high attenuation regions of an image than in low attenuation regions of an image.

Figure 16:
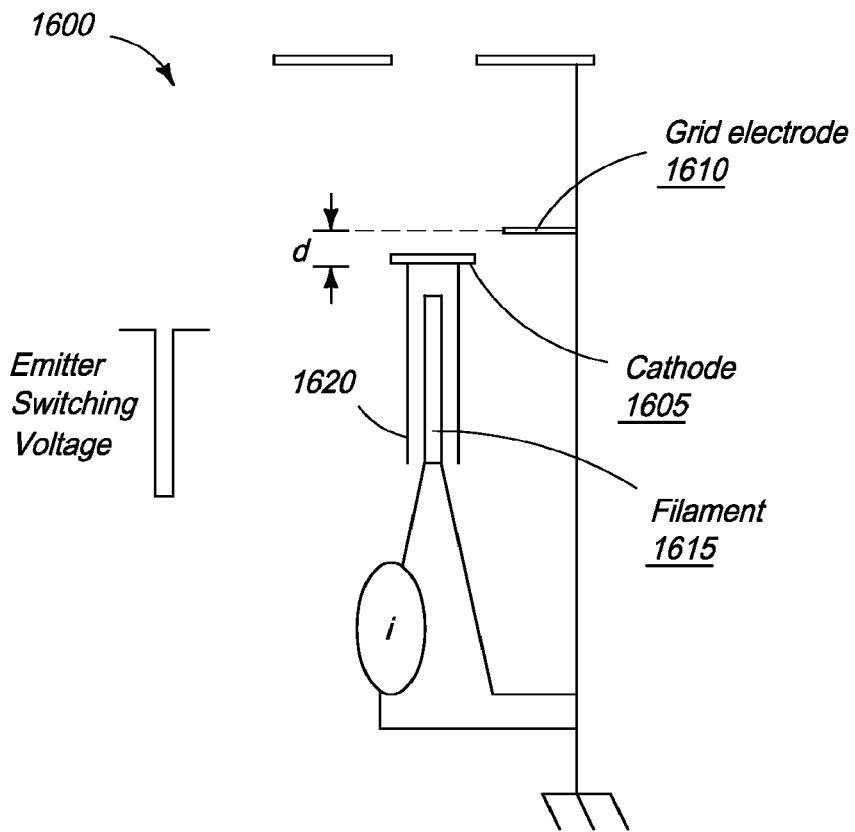
FIG. 16 shows an embodiment of the electron gun operated in space charge limited mode during operation of the system of FIG. 1.

Therefore, to maximize imaging performance, the X-ray scanner of the present invention further uses a well controlled space charge limited electron gun 1600 as shown in FIG. 16. As described earlier with reference to FIGS. 1 and 2, the X-ray scanner of the present invention utilizes a plurality of individual electron sources. To minimize variation between output source intensity of each electron gun, the X-ray scanner electron gun 1600 is operated in a space charge limited mode. Here, the electron emitter 1620 is operated with a high electron yield but the allowable emitted signal is determined by two controllable parameters: (a)

geometry and (b) extraction field. In one embodiment, the two parameters are the only two parameters used to determine the allowable emitted signal.

Referring to FIG. 16, it is observed that with a typical cathode 1605 to grid electrode 1610 distance 'd' of 0.5 mm, a variation of the order of 20 μm in this distance 'd' leads to a variation in beam current of only a few percent. However, variation in electron gun brightness is strongly affected by variation in the tolerance in positioning of the filament 1615 within the cathode 1605, on the thickness of the filament wire and on the distribution of thermal packing that may exist around the filament 1615. Considering the aforementioned aspects, in one embodiment, the X-ray scanner of the present invention is optimized to achieve less than 5% variation in brightness between individual electron emitters/sources 1620.

Thermal Load on X-Ray Tube Target

Thermal load on X-ray tube target of the X-ray scanner of the present invention is minimized to allow high power operation over extended operating periods. As a first measure, this thermal load minimization is achieved by having a large, distributed, anode where only small sections of the anode are irradiated by an electron beam at any one time and that too only for very short durations. Still, for example, a distributed anode with an irradiation time of 80 μs per source point results in an increase in localized temperature at the central point of the electron irradiation spot by around 200 degrees. Thus, as a second measure, a coolant fluid is passed around the anode such that the coolant is capable of extracting the total power that is driven into the anode (2.4 kW for a system operating at 160 kV, 20 mA). As a result, the anode is maintained at a temperature which is substantially constant over extended operating periods. The coolant fluid is selected to have good thermal transfer properties and low viscosity with a high ionisation threshold. Coolant flow rate is maintained to establish turbulent flow in the coolant pipe in order to maximise thermal transfer from the anode into the coolant fluid.

Thermal Load on X-Ray Detectors

Scintillation efficiency of X-ray detectors as well as leakage current of photodiodes (when operated in reverse bias condition) of the detectors varies with temperature. Therefore, the X-ray scanner of the present invention provides cooling of its X-ray detectors to maintain a constant operating temperature independent of ambient conditions, thereby stabilizing the reconstructed voxel values resulting in high quantitative accuracy of X-ray image.

Figure 17:
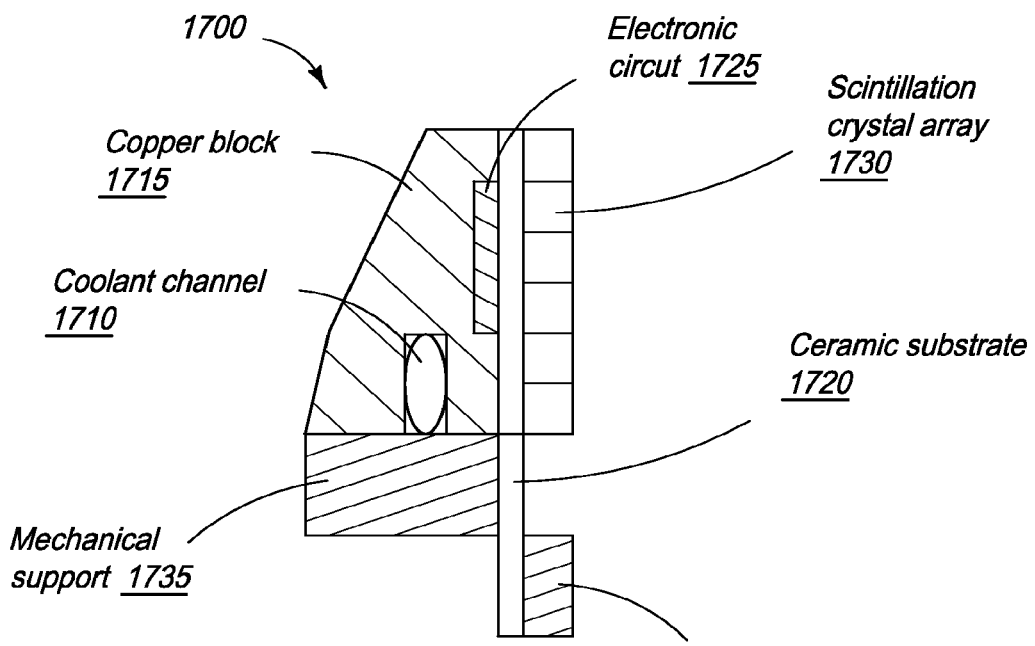
FIG. 17 shows an embodiment of the cooling system for controlling temperature of detectors of the system of FIG. 1.

FIG. 17 shows an embodiment of the cooling system for controlling temperature of detectors 1700 of the X-ray scanner of the present invention. As shown, a coolant channel 1710 is interfaced with a copper block 1715 that has high thermal conductivity supported using mechanical support 1735. Readout electronics 1725, located at the back of ceramic substrate 1720 is placed in a recess in the copper block 1715 and is thermally connected to the cooled copper block 1715 using a suitable heat sinking compound with high thermal conductivity. The ceramic substrate 1720 is then placed in direct contact with the copper block 1715, again using a suitable heat sink compound to maximize thermal connection between the ceramic substrate 1720 and the copper block 1715. Since ceramic materials, such as high density alumina, have good thermal properties therefore the photodiode and crystal 1730 are maintained at a temperature which is close to that of the copper block 1715. The entire detector assembly 1700 is placed within a light tight, electrically conductive and environmentally sealed enclosure, such as one fabricated using carbon fibre composite materials, and includes a low density connector 1740. By controlling the temperature of the coolant fluid within a range of +1 degree, a similar level of temperature control is maintained at the detector. This thermal control results in high level of stability of the reconstructed image, and typically better than 0.1%.

Referring back to FIGS. 1 and 2, in some situations, such as for maintenance or for the purposes of passing a specific regulatory performance requirement, it can be beneficial to constrain the switching of the source points 12 in the X-ray system to a sequence that is suited to other imaging methods. As an example, a single one of the source points 12 may be switched on continuously without any further source points in the scanning sequence. In this case, as the conveyor 22 scans past the stationary X-ray fan-beam, a two-dimensional image data set is built up, from which a two dimensional image can be generated.

Figures 5, 6:
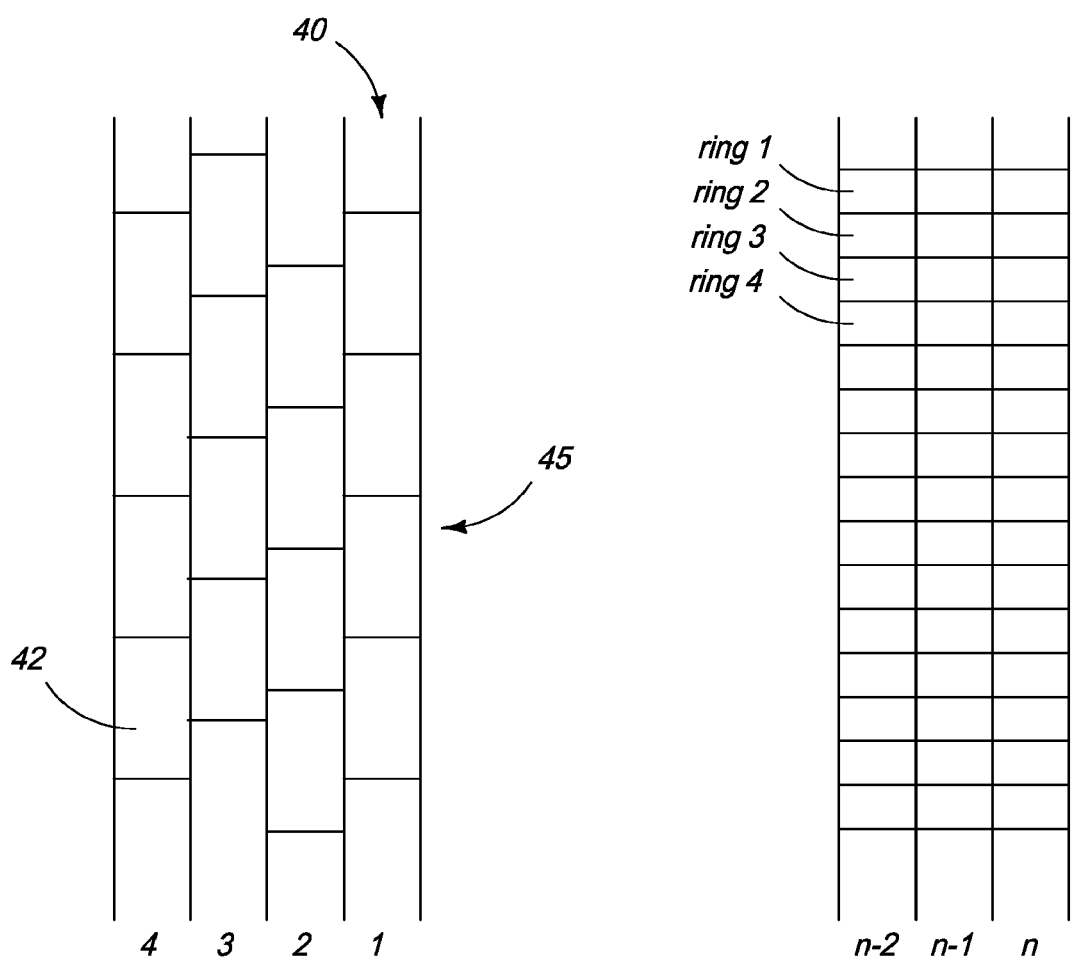
FIG. 5 shows a detector array in a scanner according to a further embodiment of the invention.
FIG. 6 shows a part of an image produced using the detector array of FIG. 5.

As an enhancement of this application, the detector rings may be configured as shown in FIG. 5. By way of example, a sensor with four detector rings 40 is shown in which the centre of the detectors 42 in each ring is shifted by ¼ of a detector spacing with reference to its adjacent rings. Data is collected from each ring 40 of sensors after the conveyor has moved a distance equal to the width of one sensor ring in the scan direction 45. Referring to FIG. 6, image data from ring 1 is then interposed with data from ring 2 after one time slice, with data from ring 3 after two time slices and with data from ring 4 after three time slices and the combined data is used to provide one line of the two-dimensional projected image. Note that the vertical pixel sampling rate is in the two dimensional image is in this example four times better than the horizontal pixel sampling rate.

An improvement in horizontal pixel sampling rate can also be achieved by sampling more rapidly with respect to the conveyor velocity than just by sampling once every one detector spacing, i.e. by performing more than one scan cycle in the time taken for the object to move a distance equal to the width of the detector ring 40 of FIG. 5.

In a related scanning mode, a sequence may be generated in which X-ray tube source points are activated over a small range of angles, typically over 10 degrees, at a rate such that all of the chosen source points are activated individually in the time taken for the conveyor to travel one detector spacing. For a detector dimension of 5 mm, a source point located every 1 degree and a conveyor speed of 0.5 m/s, each individual projection will be collected in 1 ms. In this way, a set of two-dimensional projection images are acquired, one for each selected source point.

A graphical user interface may then be provided which enables the operator to view each image in turn under control of a suitable input device such as a mouse or a pair of buttons, and to rapidly flip between images from adjacent source points as the input device is actuated. The result is a "rocking two-dimensional image" in which the object under inspection appears to rotate back and forth about the central axis of the scanning tunnel in the direction parallel to the conveyor motion under the control of the operator. This rocking image provides a powerful method by which the operator can easily perceive depth information about objects within the object under inspection.

It is clear that the data for the above two scanning modes exists within the data set that is typically collected during data acquisition for a three-dimensional tomographic image reconstruction in the system of FIG. 1, and this two-dimensional image data can advantageously be displayed alongside the full three-dimensional data set.

A high speed three-dimensional X-ray scanning system as described with reference to FIGS. 1 and 2 can be deployed for screening baggage and cargo in these, and a number of other ways.

Figure 7:
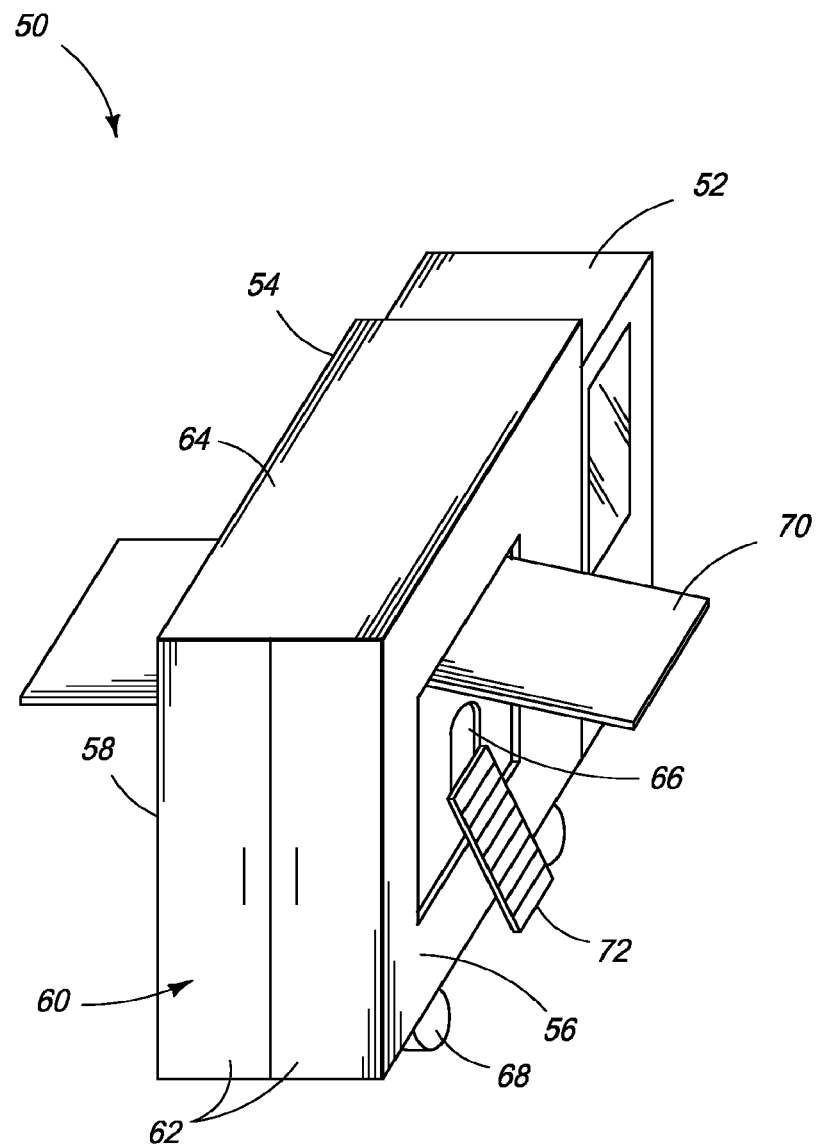
FIG. 7 is a schematic view of a scanning system according to one embodiment of the invention.

FIG. 7 shows a high speed 3D X-ray scanning system, such as that of FIG. 1, located in a vehicle 50 according to a further embodiment of the invention. Due to the lack of moving parts in this X-ray system, it is practical to locate the equipment within a vehicular platform within which the equipment is subject to significant mechanical shock. Such shock does not mechanically misalign the X-ray system which is a common failing of known systems.

The scanning equipment is very compact due to the lack of a mechanical gantry to rotate the source and detector assembly as is required in known X-ray tomography systems. The scanning equipment is of low power consumption compared to known mechanical X-ray tomography systems due to the lack of motor drive components.

In this mobile configuration, the vehicle 50 includes a cab 52 and a body 54 which has two side walls 56, 58, a rear end 60 having doors 62 therein, and a roof 64. Each of the side walls 56, 58 has an aperture 66 in it and a scanner, such as that of FIG. 1, is located within the vehicle body 54. One end of the conveyor is located close to one of the apertures 66 which forms an input aperture, and the other end of the conveyor is located close to the other aperture which forms an exit aperture. The X-ray scanner is advantageously located close to the back wheels 68. Side panels 70 are hingedly attached to each of the two side walls of the vehicle, one over each of the apertures 66, which can be opened to expose the scanning tunnel entrance and exit. Additional input and exit conveyors 72 are provided and removably connectable to the sides of the vehicle. These conveyors can be ramped to allow baggage and cargo to be loaded into the scanner and unloaded from a safe height (typically less than 1.2 m) with some protection from the weather afforded by the open side panels 70 which can be supported in an open condition so as to extend over, and thereby cover, the input and exit conveyors 72.

An operator inspection workstation can be located adjacent to the driver in the cab 52 at the front of the vehicle or adjacent to the equipment itself in the body 54 at the rear of the vehicle.

Figure 8:
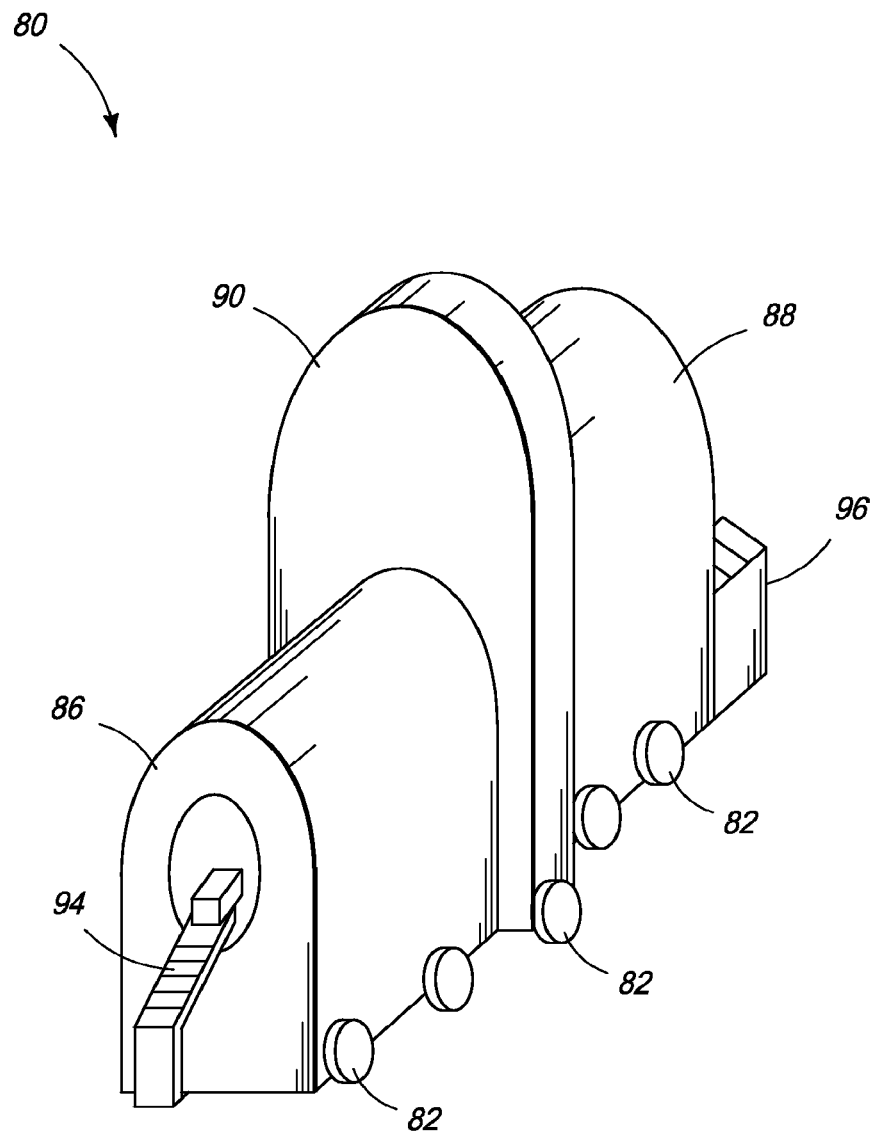
FIG. 8 is a schematic view of a scanning system according to one embodiment of the invention.
Figure 9:
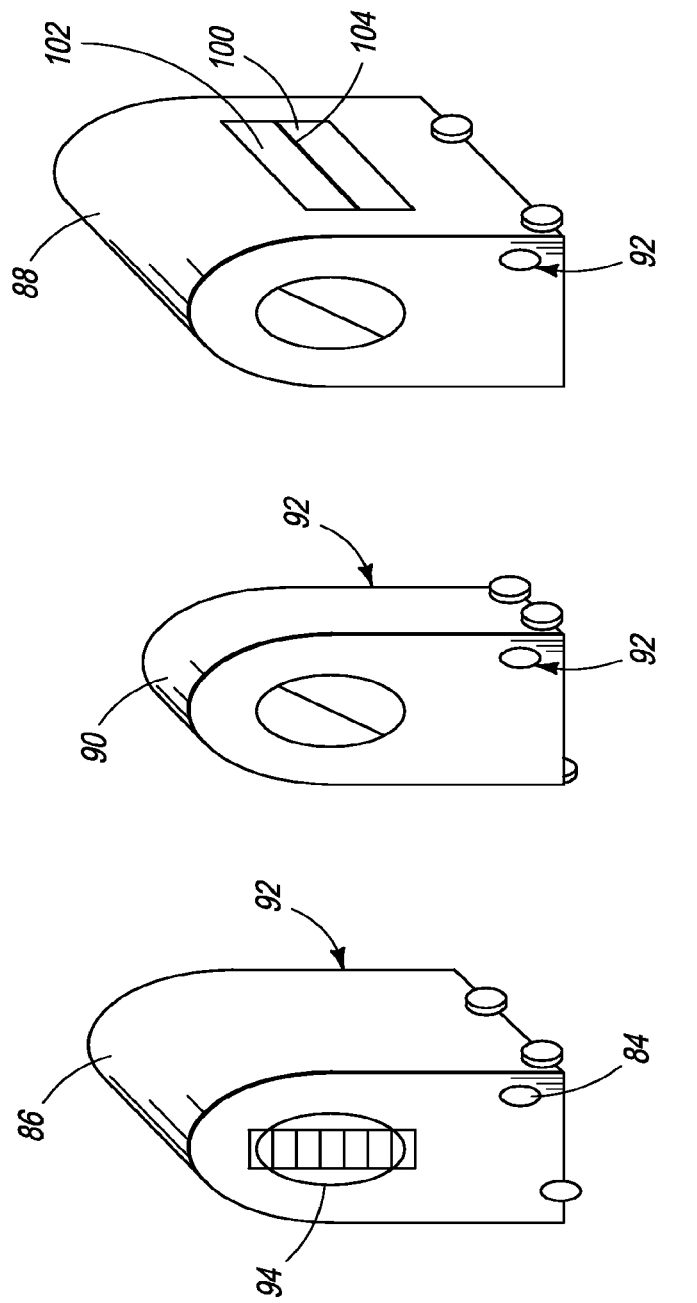
FIG. 9 is a view of the system of FIG. 8 split into its constituent parts.

In a further embodiment of the invention, the X-ray system may be constructed on a wheelable chassis as shown in FIGS. 8 and 9, where FIG. 9 is an exploded view of the chasis of FIG. 8. Referring now to FIGS. 8 and 9 simultaneously, the chassis 80 includes lockable wheels 82. When the wheels are unlocked, the system may be wheeled easily from one location to another. When at its new location, the unit can be fixed in position by locking its wheels 82. A mains power cable 84 is used to obtain electrical power from a power outlet adjacent to the chosen scanning site.

To allow the system 80 to be moved between various levels of a building, the scanner may be easily and quickly separated into three parts: an inlet tunnel section 86, an exit tunnel section 88 and a scanner section 90 as shown in FIG. 9, to allow it to be moved from one level in the building to another using an elevator. Each section is designed to be self contained and electrical connectors 92 are provided on both sides of the scanner section 90 and on the inner end of each of the other sections 86, 88, making the system connectorized such that when the three sections are brought together, electrical connectors on adjoining electrical interface plates mate to render the system functional.

To save space, in-feed and out-feed conveyor sections 94, 96 fold up to a stowed position against the front face of their respective tunnel sections 86, 88 and can be dropped back down into an in-use position once the system has been manoeuvred to its required location.

An operator workstation 100 is also advantageously located on one or more of the tunnel sections 86, 88 such that the necessary computer monitor 102 and keyboard assembly 104 are arranged to fold down from the equipment itself in order to minimise cabling and to minimise down time between system relocation.

Figure 10:
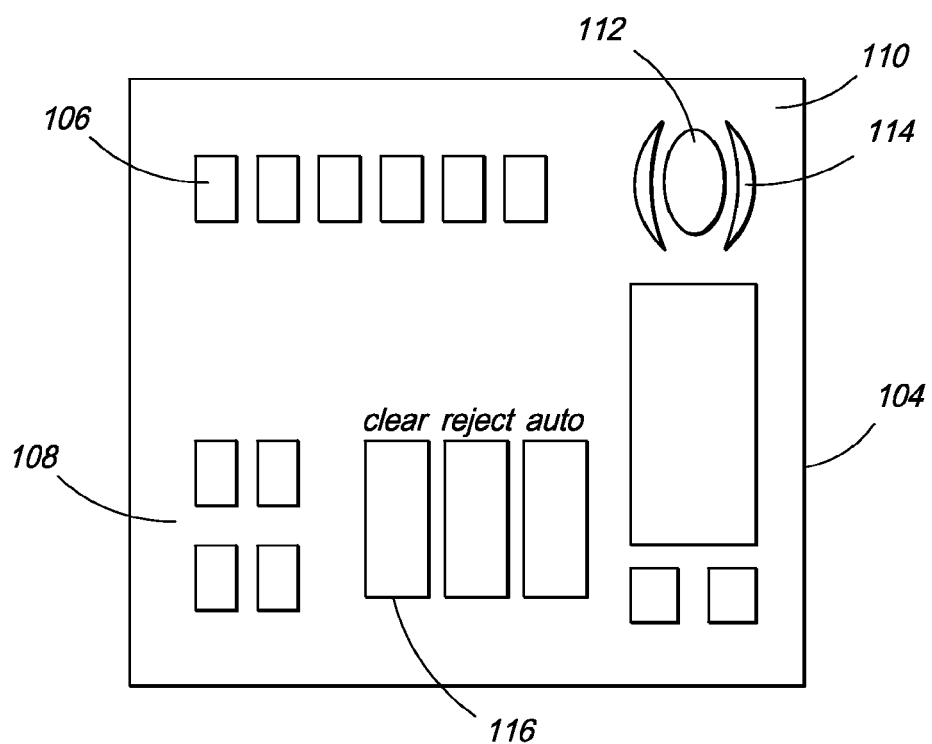
FIG. 10 is a front view of a user input panel of the embodiment of FIG. 9.

Referring to FIG. 10, keyboard 104 which may be provided with the system, but may be used in other suitable systems, makes interaction with the X-ray image straightforward. The image can be displayed on the computer monitor and manipulated by means of the keyboard 104.

In one embodiment, the keyboard 104 of FIG. 10 comprises a plurality of dedicated view select buttons 106 each of which the operator may use to bring up a standard view of the item under inspection. Standard views include a 2D projection image, a 3D interactive image, one or more pre-rendered 3D views from standard orientations and/or a rocking 2D image. A second group of buttons 108 allow the operator to select from a group of look-up tables for image colouring. Example look-up tables include greyscale (black to white), inverse greyscale (white to black), pseudo colour and materials specific colours based on dual energy materials discrimination and X-ray scatter imaging. A further group of controls 110 allow the user to interact with the image data using a trackball 112 and select buttons 114 or a track-pad and select buttons depending on user preference. A final group of buttons 116 allow the used to mark the image as being clear following inspection, to mark the image as being rejected following inspection, and to run an automated sequence of image displays which show image data for the item under inspection in a standardised preset sequence of views as a mixture of static 3D rendered images and one or more dynamic 3D rendered views.

Referring back to FIG. 9, typically, a single image display monitor 102 is used in order to view the X-ray image data. In some situations, a second computer monitor may be provided in order to show information about a related network of X-ray systems and other data relevant to the article under inspection such as passenger data, manifest data, destination of the article under inspection, shipping agent and carrier.

Figure 11:
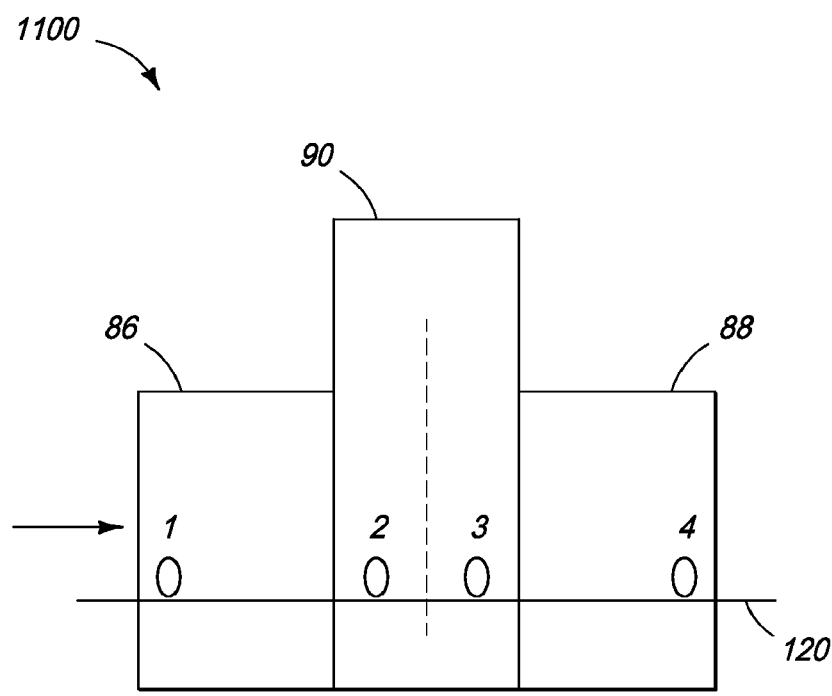
FIG. 11 is a longitudinal section through the system of FIG. 8.

Referring now to FIG. 11, in this embodiment of the present invention, the X-ray system 1100 is provided with audible and visible alarms. The use of audible alarms is minimised to prevent excess noise in the operating environment, however audible sounders are provided to indicate if an object has become stuck within the system. Visual alarms are provided to indicate when the X-ray beam is turned on and when the X-ray beam is turned off. The system 1100 is provided with means to turn the X-ray beam on and off automatically depending on whether an item is present to be inspected or not. This is achieved simply and inexpensively through the use of sensors, such as infra-red sensors 1 through 4, which are located at suitable positions along the length of the conveyor 120 as shown in FIG. 11. In this case there are two sensors in each tunnel section 86, 88 located at different distances from the scanner image volume. Sensors 1 and 2 are in the inlet tunnel section 86, with sensor 1 further from the scanner, and Sensors 3 and 4 are located in the exit tunnel section 88 with sensor 4 further from the scanner. When an object enters the inspection tunnel in the section 86, it breaks light beam 1. The object continues to move down the tunnel until it reaches Sensor 2. Sensor 1 continues to measure the length of the bag, the length being determined at the point when the output of Sensor 1 returns to normal. When Sensor 2 sees the object, it turns on the X-ray beam. The X-ray beam is kept on until the trailing edge of the object passed through Sensor 3 at which point the X-ray beam will be turned off unless a second object is about to pass Sensor 2. In this case, the beam is kept on until the second object has been scanned. Sensor 4 assists the transfer of the object out from the X-ray system 1100 to a following baggage handling system or other cargo handling system. Further visual indicators warn of the status of safety interlocks, of electrical power and other machine parameters as appropriate.

In one embodiment, the X-ray system 1100 is also provided with a Human Machine Interface. This comprises a video screen through which is provided dynamic status information on the scanning process (including the locations of objects to be scanned within the system), statistical information on the quantity and type of objects scanned together with inspection results and machine status information including software and hardware revision levels, electrical, computational, X-ray and sensor sub-system status indication. In one embodiment, the Human Machine Interface is advantageously provided with a touch screen interface, as is known to those of ordinary skill in the art, with the requirement for an operator to enter a security code in order to access some elements of the available information.

It will be appreciated that various above-disclosed embodiments, other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims. In particular, it should be appreciated that these all operative numbers represent an exemplary range and the present invention encompasses ranges that represent improvements, including higher resolution, improved signal to noise ratio, lower voltage, and more rapid conveyor speeds, relative to the numbers shown.

I claim:

1. An X-ray scanning system comprising:
   a plurality of X-ray sources arranged at least partially around an imaging volume, wherein each of the plurality of X-ray sources is stationary during operation;
   an array of X-ray detectors arranged at least partially around the imaging volume and configured to output detector signals in response to detecting X-rays emitted from each of the plurality of X-ray sources;
   a conveyor configured to convey an object through the imaging volume in a scan direction; and
   at least one processor configured to process the detector signals to produce an image data set defining a three-dimensional image of the object, wherein the image comprises a plurality of voxels, wherein each voxel of the plurality of voxels has a dimension in the scan direction that is equal to, or less than, 5 mm.

2. The X-ray scanning system of claim 1, further comprising a coolant pipe configured to direct coolant toward a portion of at least one anode of the plurality of X-ray sources.

3. The X-ray scanning system of claim 1, wherein the conveyor is configured to move at a speed in a range of 0.25 m/s to 1.0 m/s.

4. The X-ray scanning system of claim 1, wherein the conveyor is configured to move at a speed that is at least 0.1 m/s.

5. The X-ray scanning system of claim 1, wherein each voxel of the plurality of voxels has a dimension in the scan direction size is equal to, or less than, 4 mm.

6. The X-ray scanning system of claim 1, wherein each voxel of the plurality of voxels has a dimension in the scan direction that is equal to, or less than, 3 mm.

7. The X-ray scanning system of claim 1, wherein each voxel of the plurality of voxels has a dimension in the scan direction that is equal to, or less than, 2 mm.

8. The X-ray scanning system of claim 1, wherein each voxel of the plurality of voxels has a dimension in the scan direction that is equal to, or less than, 1.1 mm.

9. The X-ray scanning system of claim 1, wherein, in each direction orthogonal to the scan direction, each voxel of the plurality of voxels has a dimension that is equal to, or less than, 5 mm.

10. The X-ray scanning system of claim 1, wherein, in each direction orthogonal to the scan direction, each voxel of the plurality of voxels has a dimension that is equal to, or less than, 4 mm.

11. The X-ray scanning system of claim 1, wherein, in each direction orthogonal to the scan direction, each voxel of the plurality of voxels has a dimension that is equal to, or less than, 3 mm.

12. The X-ray scanning system of claim 1, wherein, in each direction orthogonal to the scan direction, each voxel of the plurality of voxels has a dimension that is equal to, or less than, 2 mm.

13. The X-ray scanning system of claim 1, wherein, in each direction orthogonal to the scan direction, each voxel of the plurality of voxels has a dimension that is equal to, or less than, 1.1 mm.

14. The X-ray scanning system of claim 1, wherein the at least one processor is further configured to process the detector signals to produce an image data set defining a two-dimensional image of the object.

15. The X-ray scanning system of claim 14, further comprising a graphical user interface configured to concurrently display both the two-dimensional image and the three-dimensional image.

16. The X-ray scanning system of claim 1, wherein the at least one processor is configured to generate a first two-dimensional image associated with detected X-rays from a first X-ray source of the plurality of X-ray sources and a second two-dimensional image associated with detected X-rays from a second X-ray source of the plurality of X-ray sources, wherein the second X-ray source is adjacent the first X-ray source.

17. The X-ray scanning system of claim 16, further comprising a graphical user interface configured to display the first two-dimensional image and the second two-dimensional image as a rocking two-dimensional image that appears to rotate back and forth about a central axis of the scanning volume.

18. The X-ray scanner system of claim 1, wherein the plurality of X-ray sources is arranged in a plane perpendicular to the scan direction.

19. The X-ray scanner system of claim 1, wherein the detector array is offset from the plurality of X-ray sources in the scan direction.

20. The X-ray scanner system of claim 1, further comprising a controller configured to activate each of the plurality of X-ray sources at least once in a predetermined sequence over a scan cycle.

21. The X-ray scanner system of claim 1, further comprising coolant in thermal communication with at least one detector of the array of X-ray detectors.

22. An X-ray scanning system comprising:
- a plurality of X-ray sources arranged at least partially around an imaging volume and configured to remain stationary during operation;
- an array of X-ray detectors arranged at least partially around the imaging volume and configured to output detector signals in response to detecting X-rays emitted from each of the plurality of X-ray sources;
- a conveyor configured to convey an object through the imaging volume in a scan direction, wherein the conveyor is configured to move at a speed that is at least 0.1 m/s;
- at least one processor configured to process the detector signals to produce a first image data set that defines a tomographic image of the object and produce a second image data set that defines a two-dimensional image of the object; and
- a graphical user interface configured to display at least one of the tomographic image or two-dimensional image.

23. The X-ray scanning system of claim 22, further comprising a coolant pipe configured to direct coolant toward a portion of at least one anode of the plurality of X-ray sources.

24. The X-ray scanning system of claim 22, wherein the tomographic image comprises a plurality of voxels and wherein each voxel of the plurality of voxels has a dimension in the scan direction that is equal to, or less than, 5 mm.

25. The X-ray scanning system of claim 22, wherein each voxel of the plurality of voxels has a dimension in the scan direction that is equal to, or less than, 4 mm.

26. The X-ray scanning system of claim 22, wherein each voxel of the plurality of voxels has a dimension in the scan direction that is equal to, or less than, 3 mm.

27. The X-ray scanning system of claim 22, wherein each voxel of the plurality of voxels has a dimension in the scan direction that is equal to, or less than, 2 mm.

28. The X-ray scanning system of claim 22, wherein each voxel of the plurality of voxels has a dimension in the scan direction that is equal to, or less than, 1.1 mm.

29. The X-ray scanning system of claim 22, wherein, in a direction orthogonal to the scan direction, each voxel of the plurality of voxels has a dimension that is equal to, or less than, 5 mm.

30. The X-ray scanning system of claim 22, wherein, in a direction orthogonal to the scan direction, each voxel of the plurality of voxels has a dimension that is equal to, or less than, 4 mm.

31. The X-ray scanning system of claim 22, wherein, in a direction orthogonal to the scan direction, each voxel of the plurality of voxels has a dimension that is equal to, or less than, 3 mm.

32. The X-ray scanning system of claim 22, wherein, in a direction orthogonal to the scan direction, each voxel of the plurality of voxels has a dimension that is equal to, or less than, 2 mm.

33. The X-ray scanning system of claim 22, wherein, in a direction orthogonal to the scan direction, each voxel of the plurality of voxels has a dimension that is equal to, or less than, 1.1 mm.

34. The X-ray scanning system of claim 22, wherein the graphical user interface is further configured to concurrently display both the two-dimensional image and the tomographic image.

35. The X-ray scanning system of claim 22, wherein the at least one processor is configured to generate a first two-dimensional image associated with detected X-rays from a first X-ray source of the plurality of X-ray sources and a second two-dimensional image associated with detected X-rays from a second X-ray source of the plurality of X-ray sources, wherein the second X-ray source is adjacent the first X-ray source.

36. The X-ray scanning system of claim 35, wherein the graphical user interface is further configured to display the first two-dimensional image and the second two-dimensional image as a rocking two-dimensional image that appears to rotate back and forth about a central axis of the scanning volume.

37. The X-ray scanner system of claim 22, wherein the plurality of X-ray sources is arranged in a plane perpendicular to the scan direction.

38. The X-ray scanner system of claim 22, wherein the detector array is offset from the plurality of X-ray sources in the scan direction.

39. The X-ray scanner system of claim 22, further comprising a controller configured to activate each of the plurality of X-ray sources once in a predetermined sequence over a course of a scan cycle.

40. The X-ray scanner system of claim 22, further comprising coolant in thermal communication with at least one detector of the array of X-ray detectors.

41. An X-ray scanning system comprising:
- a plurality of X-ray tubes arranged at least partially around an imaging volume and configured to remain stationary during operation;
- an array of X-ray detectors arranged at least partially around the imaging volume and configured to output detector signals in response to detecting X-rays emitted from each of the plurality of stationary X-ray tubes;
- a conveyor configured to convey an object through the imaging volume in a scan direction;
- at least one processor configured to process the detector signals to produce a first image data set that defines a three-dimensional image of the object;
- a controller configured to activate each of the plurality of stationary X-ray tubes at least once over a scan cycle; and
- a graphical user interface configured to display the three-dimensional image.

42. The X-ray scanning system of claim 41, wherein the conveyor is configured to move at a speed that is at least 0.1 m/s.

43. The X-ray scanning system of claim 41, wherein the at least one processor is configured to further produce a second image data set that defines a two-dimensional image of the object.

44. The X-ray scanning system of claim 43, wherein the graphical user interface configured to display the two-dimensional image together with the three-dimensional image.

45. The X-ray scanning system of claim 41, wherein the three-dimensional image comprises a plurality of voxels and wherein each voxel of the plurality of voxels has a dimension in the scan direction that is equal to, or less than, 5 mm.

46. The X-ray scanning system of claim 45, wherein the three-dimensional image comprises a plurality of voxels and wherein each voxel of the plurality of voxels has a dimension in a direction orthogonal to the scan direction that is equal to, or less than, 5 mm.

47. The X-ray scanning system of claim 41, wherein each of the plurality of X-ray tubes comprises one or more X-ray source points.

48. The X-ray scanning system of claim 41, wherein each of the plurality of X-ray tubes comprises one or more X-ray source points.

49. The X-ray scanning system of claim 41, wherein a resolution of the three-dimensional image in the scan direction is at least 90% of a resolution of the three-dimensional image in one or more directions orthogonal to the scan direction.

50. The X-ray scanning system of claim 41, wherein a resolution of the three-dimensional image in the scan direction is within 10% of a resolution of the three-dimensional image in one or more directions orthogonal to the scan direction.

51. The X-ray scanning system of claim 41, wherein each of the plurality of stationary X-ray tubes has a voltage in a range of 100 kV to 200 kV.

52. The X-ray scanning system of claim 41, wherein each of the plurality of stationary X-ray tubes has a voltage in a range of 150 kV to 180 kV.

53. The X-ray scanning system of claim 41, wherein the at least one processor is configured to generate at least 100 reconstruction slices per second.

54. The X-ray scanning system of claim 41, wherein the at least one processor is configured to generate 100 to 1000 reconstruction slices per second.

55. The X-ray scanning system of claim 41, wherein the X-ray scanning system has a dynamic range of 1000 or more.

56. The X-ray scanning system of claim 41, wherein the three-dimensional image has a signal to noise ratio of 50 or more.

57. An X-ray scanning system comprising:
 a plurality of X-ray tubes arranged at least partially around an imaging volume and configured to remain stationary during operation, wherein each of the plurality of stationary X-ray tubes has a voltage in a range of 100 kV to 200 kV;
 an array of X-ray detectors arranged at least partially around the imaging volume and configured to output detector signals in response to detecting X-rays emitted from each of the plurality of stationary X-ray tubes;
 a conveyor configured to convey an object through the imaging volume in a scan direction, wherein the conveyor is configured to move at a speed that is at least 0.1 m/s;
 at least one processor configured to process the detector signals to produce a first image data set that defines a tomographic image of the object and to produce a second image data set that defines a two-dimensional image of the object;
 a controller configured to activate each of the plurality of stationary X-ray tubes at least once over a scan cycle; and
 a graphical user interface configured to display at least one of the tomographic image or the two-dimensional image.

58. The X-ray scanning system of claim 57, wherein the graphical user interface configured to concurrently display the two-dimensional image together and the tomographic image.

59. The X-ray scanning system of claim 57, wherein the tomographic image comprises a plurality of voxels and wherein each voxel of the plurality of voxels has a dimension in the scan direction that is equal to, or less than, 5 mm.

60. The X-ray scanning system of claim 57, wherein the tomographic image comprises a plurality of voxels and wherein each voxel of the plurality of voxels has a dimension in a direction orthogonal to the scan direction that is equal to, or less than, 5 mm.

61. The X-ray scanning system of claim 57, wherein a resolution of the tomographic image in the scan direction is at least 90% of a resolution of the tomographic image in one or more directions orthogonal to the scan direction.

62. The X-ray scanning system of claim 57, wherein a resolution of the tomographic image in the scan direction is within 10% of a resolution of the tomographic image in one or more directions orthogonal to the scan direction.

63. The X-ray scanning system of claim 57, wherein each of the plurality of stationary X-ray tubes has a voltage in a range of 150 kV to 180 kV.

64. The X-ray scanning system of claim 57, wherein the at least one processor is configured to generate at least 100 reconstruction slices per second.

65. The X-ray scanning system of claim 57, wherein the at least one processor is configured to generate 100 to 1000 reconstruction slices per second.

66. The X-ray scanning system of claim 57, wherein the X-ray scanning system has a dynamic range of 1000 or more.

67. The X-ray scanning system of claim 57, wherein the tomographic image has a signal to noise ratio of 50 or more.

68. The X-ray scanning system of claim 57, wherein each of the plurality of X-ray tubes comprises one or more X-ray source points.

* * * * *